US010849731B2

(12) United States Patent
Cully et al.

(10) Patent No.: US 10,849,731 B2
(45) Date of Patent: Dec. 1, 2020

(54) CELL ENCAPSULATION DEVICES CONTAINING STRUCTURAL SPACERS

(71) Applicants: W. L. Gore & Associates, Inc., Newark, DE (US); W. L. Gore & Associates GmbH, Putzbrunn (DE)

(72) Inventors: Edward H. Cully, Flagstaff, AZ (US); Bernadette Parsons, Newark, DE (US); Lauren Zambotti, Wilmington, DE (US); Paul D. Drumheller, Flagstaff, AZ (US)

(73) Assignees: W. L. Gore & Associates, Inc., Newark, DE (US); W. L. Gore & Associates GmbH, Putzbrunn (DE)

( * ) Notice: Subject to any disclaimer, the term of this patent is extended or adjusted under 35 U.S.C. 154(b) by 496 days.

(21) Appl. No.: 15/806,099

(22) Filed: Nov. 7, 2017

(65) Prior Publication Data
US 2018/0125632 A1 May 10, 2018

Related U.S. Application Data

(60) Provisional application No. 62/419,148, filed on Nov. 8, 2016.

(51) Int. Cl.
*A61F 2/02* (2006.01)
*A61L 27/36* (2006.01)
(Continued)

(52) U.S. Cl.
CPC ............. *A61F 2/022* (2013.01); *A61L 27/16* (2013.01); *A61L 27/36* (2013.01); *A61M 5/00* (2013.01);
(Continued)

(58) Field of Classification Search
CPC .. A61F 2/0077; A61F 2002/0091; A61F 2/02; A61F 2210/00; A61F 2250/0067; A61F 2002/0081; A61F 2002/009; A61F 2210/0004; A61F 2210/0014; A61F 2210/0071; A61F 2210/0076; A61F 2240/001; A61F 2250/0068; A61F 2/022;
(Continued)

(56) References Cited

U.S. PATENT DOCUMENTS

| 5,425,928 A | 6/1995 | Martin et al. |
| 5,626,561 A | 5/1997 | Butler et al. |
(Continued)

FOREIGN PATENT DOCUMENTS

| WO | WO96/32076 | 10/1996 | |
| WO | WO-9632076 A1 * | 10/1996 | ............. C08L 27/18 |
| WO | WO2014/173441 | 10/2014 | |

OTHER PUBLICATIONS

International Search Report of PCT/US2017/060497 dated Feb. 8, 2018 and dated Feb. 19, 2018.

*Primary Examiner* — Jason E Flick
(74) *Attorney, Agent, or Firm* — Amy L. Miller

(57) ABSTRACT

An implantable containment apparatus for receiving and retaining a plurality of cells for insertion into a patient, such as into a tissue bed, is disclosed. The device includes a chamber having structural spacers therein to maintain an average distance between the first interior surface and the second interior surface of the chamber and to define at least one reservoir space for the placement of cells within the chamber.

71 Claims, 20 Drawing Sheets

(51) Int. Cl.
    *C12N 5/00*         (2006.01)
    *A61M 5/00*        (2006.01)
    *A61L 27/16*       (2006.01)
    *A61M 31/00*      (2006.01)
    *A61F 2/00*         (2006.01)

(52) U.S. Cl.
    CPC ......... *A61M 31/002* (2013.01); *C12N 5/0012* (2013.01); *A61F 2002/009* (2013.01); *A61F 2002/0081* (2013.01); *A61F 2210/0004* (2013.01); *A61F 2210/0014* (2013.01); *A61F 2210/0071* (2013.01); *A61F 2210/0076* (2013.01); *A61F 2240/001* (2013.01); *A61F 2250/0068* (2013.01); *A61M 2202/097* (2013.01)

(58) Field of Classification Search
    CPC .......... A61L 27/00; A61L 29/00; A61L 27/16; A61L 27/36; A61M 2202/00; A61M 2202/0007; A61M 2202/09; A61M 31/00; A61M 2202/097; A61M 31/002; A61M 5/00; C12N 5/00; C12N 5/0012
    See application file for complete search history.

(56) References Cited

U.S. PATENT DOCUMENTS

| | | |
|---|---|---|
| 5,843,069 A | 12/1998 | Butler et al. |
| 7,192,450 B2 | 3/2007 | Brauker et al. |
| 9,132,226 B2 | 9/2015 | Martinson et al. |
| 9,259,435 B2 | 2/2016 | Brown et al. |
| 2014/0257515 A1 | 9/2014 | So et al. |
| 2014/0303544 A1* | 10/2014 | Haffner ............... A61F 9/00781 604/9 |

* cited by examiner

CELL ENCAPSULATION DEVICES CONTAINING STRUCTURAL SPACERS

FIELD

The present invention relates generally to the field of medical devices and in particular, to a device containing structural spacers for encapsulating and implanting cells into a patient.

BACKGROUND

Biological therapies are increasingly viable methods for treating peripheral artery disease, aneurysm, heart disease, Alzheimer's and Parkinson's diseases, autism, blindness, diabetes, and other pathologies.

With respect to biological therapies in general, cells, viruses, viral vectors, bacteria, proteins, antibodies, and other bioactive moieties may be introduced into a patient by surgical or interventional methods that place the bioactive moiety into a tissue bed of a patient. Often the bioactive moieties are first placed in a device that is then inserted into the patient. Alternatively, the device may be inserted into the patient first with the bioactive moiety added later.

Known encapsulation devices include spacers within the lumen of the device to distribute cells within the lumen and to maintain an open space for the cells, where the spacers are in the form of free floating mesh, foams, or fabrics. These spacers can move within the lumen and aggregate, reducing their effectiveness for their intended purpose. Other cell encapsulation devices include a lumen and internal welds. The internal welds serve to compartmentalize the lumen to better distribute the cells within the lumen, but does so by compressing the device in one or more locations, which reduces the interior volume of the lumen. Such a reduction in the interior volume may cause discontinuity and interruption of the outer vascularizing surface.

There remains a need for devices that encapsulate cells and/or other biological moieties, where the devices are structurally reinforced to prevent deformation and deflection while the retaining device cross-sectional thickness and outer surface.

SUMMARY

The terms "invention," "the invention," "this invention" and "the present invention," as used in this document, are intended to refer broadly to all of the subject matter of this patent application and the claims below. Statements containing these terms should be understood not to limit the subject matter described herein or to limit the meaning or scope of the patent claims below. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings, and each claim.

Described herein are cell encapsulation devices that include first and second layers sealed along a portion of their periphery, a chamber located between the first and second layers, and structural spacers disposed within the chamber to separate the first and second layers. The chamber includes first and second interior surfaces that are spaced apart by a distance. Additionally, the structural spacers maintain an average distance between the first and second interior surfaces. In some embodiments, the first interior surface, the second interior surface, and the structural spacers define a reservoir space for the placement and retention of cells within the chamber. The cell encapsulation devices further include at least one port in fluid communication with the reservoir space. The port may allow access between the first and second layers or through the first and second layers to the chamber so that a fluid containing the biological moiety may be delivered into the cell encapsulation device.

In some embodiments, the structural spacers define at least two reservoir spaces. For example, the structural spacers may define a plurality of reservoir spaces. In some embodiments, the plurality of reservoir spaces are interconnected. In other embodiments, at least two reservoir spaces are discrete (i.e. not interconnected).

In some embodiments, a cell encapsulation device described herein includes a port that extends through the sealed periphery of the first layer and the second layer. In alternate embodiments, the port may extend through either the first or the second layer.

In some embodiments, the first and second layers of a cell encapsulation device described herein are cell retentive layers which are impervious to cell ingrowth.

In some embodiments, the first and/or second layers are vascularizing layers. In such embodiments, the cell(s) to be inserted into the cell encapsulation device may be microencapsulated. The cells may be microencapsulated within a biomaterial of natural or synthetic origin, including, but not limited to, a hydrogel biomaterial.

In some embodiments, at least one of the first and the second layers includes a composite layer. In one embodiment, both the first and the second layers are composite layers. In some embodiments, the composite layer includes an outer porous layer and an inner porous layer disposed adjacent to the outer porous layer. The inner porous layer of a cell encapsulation device described herein may have a porosity that is less than the porosity of the outer porous layer. In some embodiments, a portion of the inner porous layer forms the first and/or the second interior surface of a cell encapsulating device as described herein.

In some embodiments, an outer porous layer of a cell encapsulation device as described herein is sufficiently porous to permit growth of vascular tissue from a patient within the pores of the outer porous layer up to, but not through, the inner porous layer. Thus, the inner porous layer is impervious to cellular ingrowth.

In some embodiments, the structural spacers of a cell encapsulation device as described herein are adhered to the inner porous layers of the first and second composite layers. In some embodiments, while the structural spacers penetrate a portion of the pores of the inner porous layers, they do not penetrate the outer porous layer so that the outer porous layer remains undisturbed to allow for cellular ingrowth.

In some embodiments, a cell encapsulation device described herein includes an outer porous layer that may be formed of alginate, cellulose acetate, polyalkylene glycols such as polyethylene glycol and polypropylene glycol, pan-vinyl polymers such as polyvinyl alcohol, chitosan, polyacrylates such as polyhydroxyethylmethacrylate, agarose, hydrolyzed polyacrylonitrile, polyacrylonitrile copolymers, polyvinyl acrylates such as polyethylene-co-acrylic acid, porous polytetrafluoroethylene (PTFE), modified porous polytetrafluoroethylene polymers, porous tetrafluoroethylene (TFE) copolymers, porous polyalkylenes such as porous polypropylene and porous polyethylene, porous polyvinylidene fluoride, porous polyester sulfone, porous polyurethanes, porous polyesters, and copolymers and combinations thereof. In some embodiments, a cell encapsulation device described herein includes an inner porous layer of porous polytetrafluoroethylene, porous polypropylene, porous polyethylene, or porous polyvinylidene fluoride.

In some embodiments, the structural spacers of a cell encapsulation device described herein maintain the average distance between the first and second interior surfaces under an applied force. Advantageously, maintaining the average distance keeps the structural shape intact and avoids deformation that may result in rupture of the device. In addition, failure to maintain the average distance may result in undesirable volume changes. Optimal spacing will vary for different cell types. If the optimal average distance between the interior surfaces is exceeded, some cells within the encapsulation device will inadvertently reside too far from the device wall to receive nutrients and other biomolecules. Cells that do not receive adequate nutrients and oxygen will die. In some embodiments, the applied force is an external compressive force, while in other embodiments, the applied force may be an internal expansive force. Thus, the structural spacers may withstand both forces to maintain the average distance.

In some embodiments, the structural spacers of a cell encapsulation device described herein are formed from a porous material. In some embodiments, the porous material is alginate, cellulose acetate, polyalkylene glycols such as polyethylene glycol and polypropylene glycol, panvinyl polymers such as polyvinyl alcohol, chitosan, polyacrylates such as polyhydroxyethylmethacrylate, agarose, hydrolyzed polyacrylonitrile, polyacrylonitrile copolymers, polyvinyl acrylates such as polyethylene-co-acrylic acid, porous polytetrafluorethylene (PTFE), porous modified polytetrafluorethylene polymers, porous tetrafluoroethylene (TFE) copolymers, porous polyalkylenes such as porous polypropylene and porous polyethylene, porous polyvinylidene fluoride, porous polyester sulfone, porous polyurethanes, porous polyesters, and copolymers and combinations thereof.

In an alternative embodiment, the structural spacers of a cell encapsulation device described herein are formed from a non-porous material. In some embodiments, the non-porous material includes polytetrafluoroethylene (PTFE), polyurethane, polypropylene, polyethylene, melt-processable fluoropolymers, such as, for example, fluorinated ethylene propylene (FEP), tetrafluoroethylene-(perfluoroalkyl) vinyl ether (PFA), an alternating copolymer of ethylene and tetrafluoroethylene (ETFE), a terpolymer of tetrafluoroethylene (TFE), hexafluoropropylene (HFP), and vinylidene fluoride (THV), polyvinylidene fluoride (PVDF), and combinations thereof. In some embodiments, the non-porous material includes fluorinated ethylene propylene, tetrafluoroethylene-(perfluoroalkyl) vinyl ether, polytetrafluoroethylene, polyurethane, polyvinylidene fluoride, and combinations thereof.

In some embodiments, a cell encapsulation device described herein includes first and second interior surfaces that each independently have a surface area. The surface area may vary depending on the size of the cells and/or implantation site and on the average distance between the first and second interior surfaces. The surface area will further depend on the specific cell therapy employed and the productivity of the cells required to meet the therapeutic need. In some embodiments, the average distance between the first and second interior surfaces is up to 50 microns. In some examples the distance between the first and second interior surfaces is at least about 50 microns (e.g., between 50 microns and 100 microns), at least 100 microns (e.g. between 100 and 150 microns), at least 150 microns (e.g., between 150 microns and 200 microns, or at least 200 microns (e.g. between 200 microns and 250 microns). In some examples, the average distance may be about 50 microns, 100 microns, 200 microns, 250 microns, at least 250 microns, or 500 microns or more. In one embodiment maintaining the average distance may place the first layer in a substantially parallel relationship with the second layer.

In some embodiments, a cell encapsulation device described herein includes structural spacers covering at least a portion of the surface area of each of the first and second interior surfaces.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 18A is a schematic illustration depicting the orientation of the components forming a cell encapsulation device by printing a thermoplastic polymer onto a cell retention layer according to embodiments described herein;

FIG. 18B is a schematic illustration of a cell encapsulation device with the structural spacers formed by the printing of a thermoplastic polymer according to embodiments described herein;

DETAILED DESCRIPTION

Figure 1:
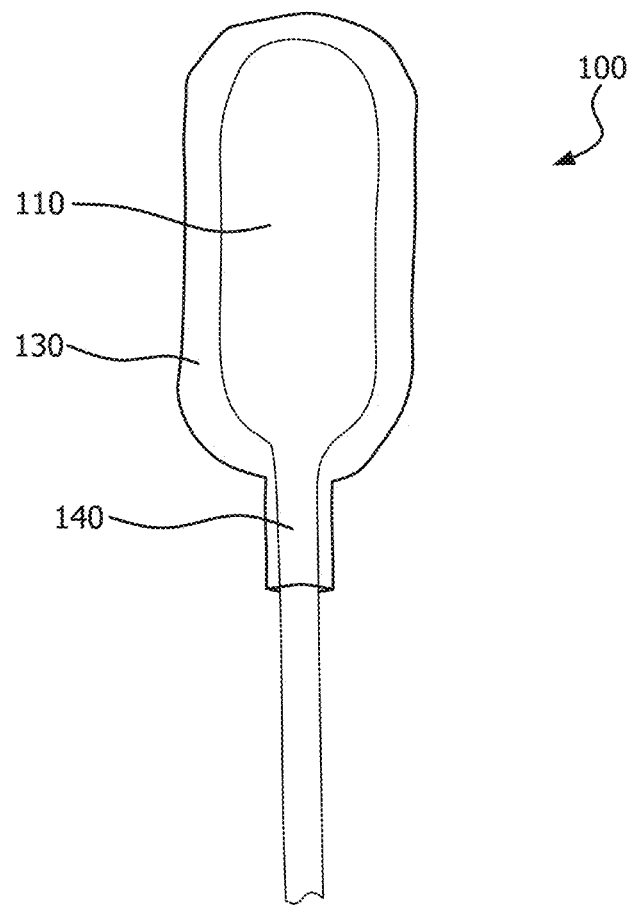
FIG. 1 is a schematic illustration of the top view of a cell encapsulation device according to embodiments described herein.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Described herein are devices for encapsulating biological moieties, where the biological moieties are implanted into a patient, such as into a tissue bed, to provide biological therapy. Also described herein are methods for forming the devices and for introducing the biological moieties into the devices. In some embodiments, the cell encapsulation device is formed of composite layers, each having an inner porous layer for the retention of biological moieties and an outer porous layer that enables vascularization and cellular ingrowth. The composite layers are spaced apart by structural spacers that define reservoir spaces for the retention of biological moieties. In other embodiments, the device may be an expanded membrane having internal structural spacers that define the reservoir spaces.

Biological moieties suitable for encapsulation and implantation using the devices described herein include cells, viruses, viral vectors, gene therapies, bacteria, proteins, polysaccharides, antibodies, and other bioactive moieties. For simplicity, herein the biological moiety is referred to as a cell, but nothing in this description limits the biological moiety to cells or to any particular type of cell, and the following description applies also to biological moieties that are not cells. Various types of prokaryotic cells, eukaryotic cells, mammalian cells, non-mammalian cells, and/or stem cells may be used with the cell encapsulation devices of the present invention. In some embodiments, the cells are microencapsulated within a biomaterial of natural or synthetic origin, including, but not limited to, a hydrogel biomaterial. In some embodiments, the cells secrete a therapeutically useful substance. Such substances include hormones, growth factors, trophic factors, neurotransmitters, lymphokines, antibodies, or other cell products which provide a therapeutic benefit to the device recipient. Examples of such therapeutic cell products include, but are not limited to, insulin, growth factors, interleukins, parathyroid hormone, erythropoietin, transferrin, and Factor VIII. Non-limiting examples of suitable growth factors include vascular endothelial growth factor, platelet-derived growth factor, platelet-activating factor, transforming growth factors, bone morphogenetic protein, activin, inhibin, fibroblast growth factors, granulocyte-colony stimulating factor, granulocyte-macrophage colony stimulating factor, glial cell line-derived neurotrophic factor, growth differentiation factor-9, epidermal growth factor, and combinations thereof. It is to be appreciated that throughout this disclosure the terms "cell" or "cells" could be replaced by "biological moiety" or "biological moieties", respectively.

One embodiment of a device for encapsulating cells is illustrated in FIG. 1. FIG. 1 is a schematic illustration of a top view of a cell encapsulation device 100 including a first (top) layer 110 and a second (bottom) layer (not shown) sealed along a portion of their periphery 130, a chamber (not shown) located between the first and second layers, and a port 140 that extends through the sealed periphery 130 and is in fluid communication with the chamber.

Figure 2:
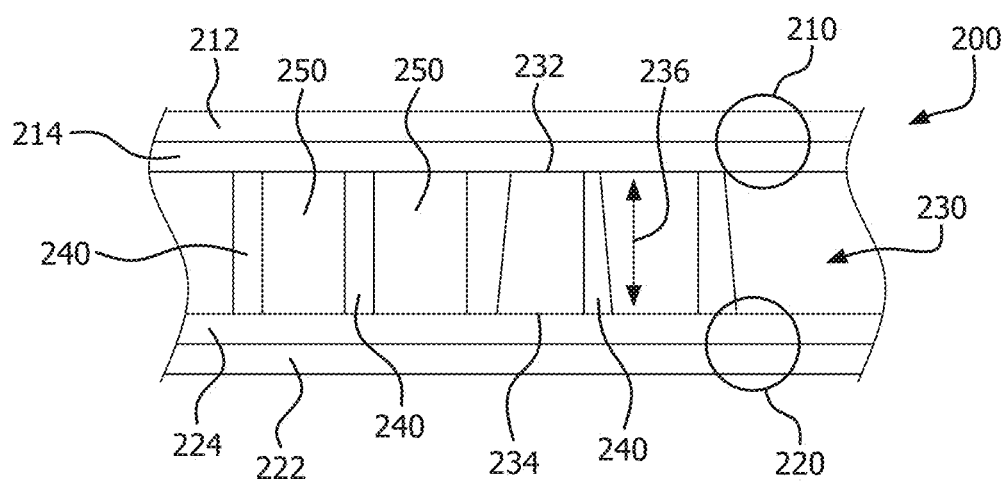
FIG. 2 is a schematic illustration of a cross-section of a cell encapsulation device according to embodiments described herein.

FIG. 2 is a schematic illustration of a cross-section of a cell encapsulation device 200 that includes a first composite layer 210 and a second composite layer 220, a chamber 230 positioned between the first and second composite layers 210, 220, structural spacers 240 disposed within the chamber 230 to separate the first and second composite layers 210, 220. The chamber 230 has first and second interior surfaces 232, 234 that are spaced apart a distance 236. The first composite layer 210 includes an outer porous layer 212 and an inner porous layer 214 disposed adjacent to the outer porous layer 212. The second composite layer 220 also includes an outer porous layer 220 and an inner porous layer 224. The outer porous layers 212, 222 of the first and second layers 210, 220 may include or be formed of the same material or different materials. Likewise, the inner porous layers 214, 224 of the first and second composite layers 210, 220 may include or be formed of the same material or different materials. In some embodiments, the inner porous layer has a porosity that is less than the porosity of the outer porous layer. Portions of the inner porous layers 214, 224 form the first and the second interior surfaces 232, 234 of the cell encapsulating device 200.

The structural spacers maintain an average distance between the first and second interior surfaces of a cell encapsulation device. The phrase "average distance", as used herein, is meant to describe the distance between the first composite layer (or first interior surface) and the second composite layer (or second interior surface) over a length and/or width (or first and second diameter or other selected dimension) in the chamber of the cell encapsulation device where the cells reside and which is substantially consistent in thickness across that dimension. As discussed below, localized regions within the length and/or width within the chamber of the cell encapsulation device where the cells reside may vary in thickness, but the average distance remains the same. As used herein, the term "chamber" is meant to define the total area within the cell encapsulation device between a first cell retentive layer (e.g., a first inner porous layer or cell retentive layer) and a second cell retentive layer (e.g., an second inner porous layer or cell retentive layer) and within the periphery of the cell encapsulation device where the placement of cells or other biological moieties occurs (or where the cells or other biological moieties reside). In some embodiments, the first interior surface 232, the second interior surface 234, and the structural spacers 240 define a plurality of reservoir spaces 250 for the placement of cells (not shown) within the chamber 230. The reservoir spaces 250 may be interconnected so as to permit the flow of cells into the various reservoir spaces 250.

Figure 3:
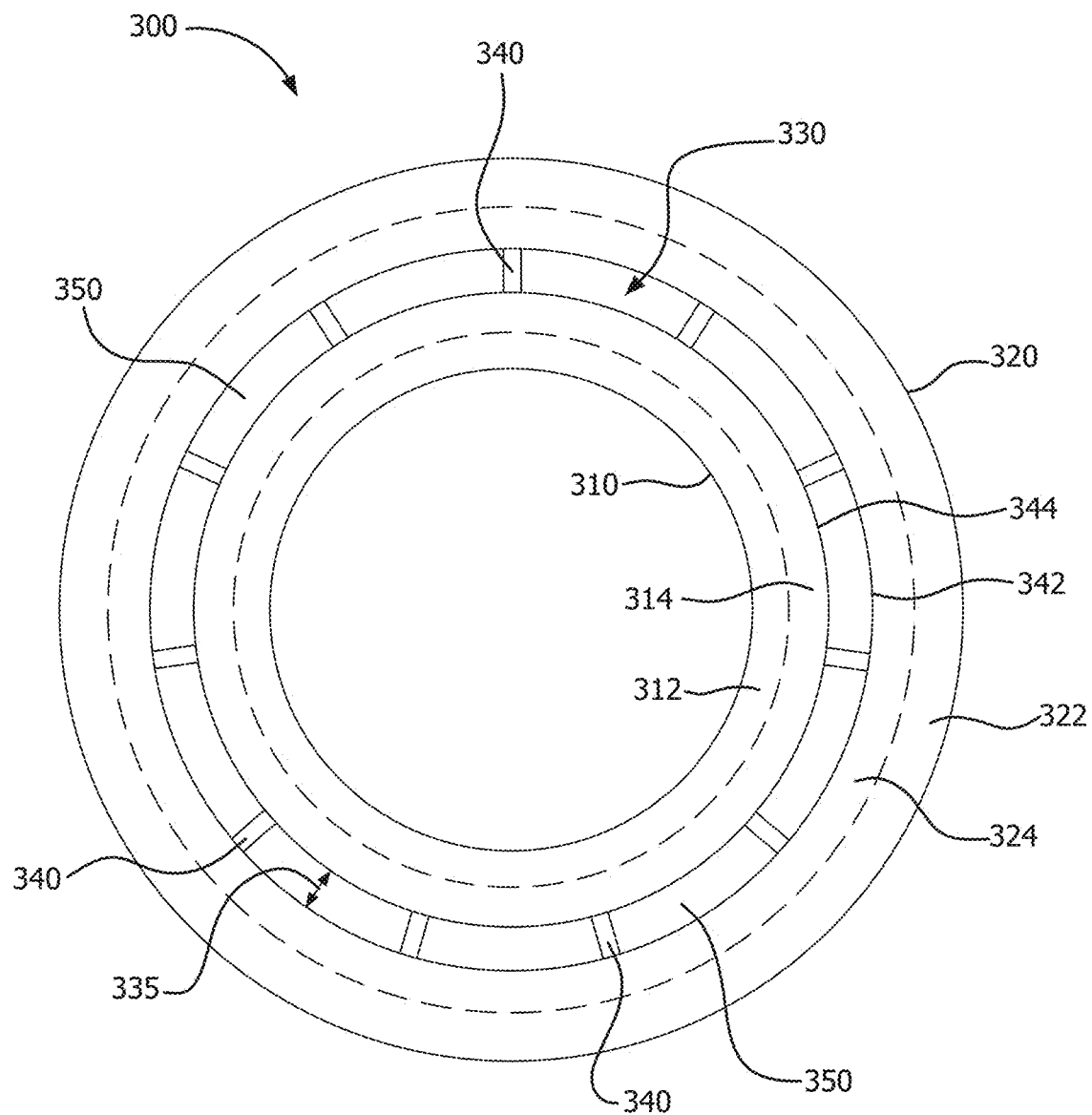
FIG. 3 is a schematic illustration of a cross-section of a tubular encapsulation device having a composite inner layer and a composite outer layer according to embodiments described herein.

FIG. 3 is a schematic illustration of a cross-section of an exemplary tubular cell encapsulation device 300 that includes an inner layer 310 and an outer layer 320, and a cell containment layer 330 positioned between the inner and outer layers 310, 320. The first composite layer 310 includes an outer porous layer 312 and an inner porous layer 314 disposed adjacent to the outer porous layer 312. The second composite layer 320 also includes an outer porous layer 322 and an inner porous layer 324. The chamber 330 is positioned between the first and second interior surfaces 342, 344, respectively, and includes structural spacers 340 that maintain a distance 335 during a geometric change of the device 300 and define a plurality of reservoir spaces for the placement of cells (or other biological moiety). The structural spacers maintain an average distance 335 from a first diameter to a second diameter. In one embodiment maintaining the separation distance 335 may place the inner layer in a substantially parallel relationship with the outer layer. The structural spacers 340 define a plurality of reservoir spaces 350 for the placement of cells (not shown) within the cell containment layer 330.

In some embodiments, the inner porous layers of the first and second layers are impervious to cell ingrowth. For example, in some embodiments, both inner porous layers have an average pore size that is sufficiently small so as to prevent vascular ingrowth. Herein, layers that restrict or prevent vascular ingrowth may be referred to as "tight" layers. The average pore size of the inner porous layer may be less than about 5 microns, less than about 1 micron, less than about 0.8 microns, less than about 0.5 microns, less than about 0.3 microns, or less than about 0.1 micron, as measured by porometry. A small pore size allows the inner porous layer to function as a cell retentive layer to keep cells disposed in the chamber inside the cell encapsulation device, yet allows nutrients and other biomolecules to enter and cell waste and therapeutic products to exit. This layer is sometimes referred to herein as a cell retentive layer.

In some embodiments, both of the outer porous layers are sufficiently porous to permit the growth of vascular tissue from a patient into the pores of the outer porous layer. One or both outer porous layers have an average pore size that is large enough to allow the ingrowth of vascular tissue. Herein, layers that have openings large enough to allow vascular ingrowth may be referred to as "open" layers. In some non-limiting examples, the pore size of the outer porous layer is greater than about 5.0 microns, greater than about 7.0 microns, or greater than about 10 microns as measured by porometry. Ingrowth of vascular tissues through the outer porous layer facilitates nutrient and biomolecule transfer from the body to the cells encapsulated in the device. This layer may be referred to herein as a vascularizing layer.

Various cell types can grow into the vascularizing layer of a porous material of cell encapsulation device as described herein. The predominant cell type that grows into a particular porous material depends primarily on the implantation site, the composition and permeability of the material, and any biological factors, such as cytokines and/or cell adhesion molecules, for example, that may be incorporated in the material or introduced through porous material(s). In some embodiments, vascular endothelium is the predominant cell type that grows into a porous material for use in a cell encapsulation device. Vascularization of the porous material by a well-established population of vascular endothelial cells in the form of a capillary network is encouraged to occur as a result of neovascularization of the material from tissues of a patient into and across the thickness of the material very close to the interior surface of the apparatus, but not across the cell retentive layer.

In some embodiments, only one of the first and second layers 210, 220 is a composite layer. For example, the first layer 210 may be a composite layer that includes an outer porous layer that is a vascularizing layer and an inner porous layer that is a cell retentive layer, while the second layer may include only a cell retentive layer. In another embodiment, neither of the first and the second layers is a composite layer, but rather only includes a cell retentive layer.

In a further embodiment, neither the first nor the second layer is a composite layer. Instead, the first and/or second layers are vascularizing layers (which permit some degree of host cell penetration and vascularization into the cell encapsulation device). In such an embodiment, the cells to be inserted into the cell encapsulation device may be microencapsulated, which provides isolation for the cells from host immune response. In some embodiments, the cells may be microencapsulated within a biomaterial of natural or synthetic origin, including, but not limited to, a hydrogel biomaterial. As a result, a separate cell retentive layer may be omitted from the cell encapsulation device.

In an embodiment where the cell encapsulation device includes only cell retentive layers and no vascularizing layer(s), the cell encapsulation device optionally could be used with a housing that is, or can be, disposed in a patient, and that is made from a vascularizing material that allows the ingrowth of vascular tissue. In some embodiments, the housing may be implanted into a patient for a period of time sufficient to allow vascularization before the cell encapsulation device is inserted into the housing. In other embodiments, the device and the housing may be inserted into a patient together.

Materials useful as an outer porous (vascularizing) layer as well as an inner porous (cell retentive) include, but are not limited to, alginate, cellulose acetate, polyalkylene glycols such as polyethylene glycol and polypropylene glycol, pan-vinyl polymers such as polyvinyl alcohol, chitosan, polyacrylates such as polyhydroxyethylmethacrylate, agarose, hydrolyzed polyacrylonitrile, polyacrylonitrile copolymers, polyvinyl acrylates such as polyethylene-co-acrylic acid, porous polytetrafluoroethylene (PTFE), porous modified polytetrafluoroethylene polymers, porous tetrafluoroethylene (TFE) copolymers, porous polyalkylenes such as porous polypropylene and porous polyethylene, porous polyvinylidene fluoride, porous polyester sulfone (PES), porous polyurethanes, porous polyesters, porous PPX (ePPX), porous ultra-high molecular weight polyethylene (eUHMWPE), porous ethylene tetrafluoroethylene (eETFE), porous vinylidene fluoride (eVDF), porous polylactic acid (ePLLA), and copolymers and combinations thereof, as well as woven or non-woven collections of fibers or yarns, or fibrous matrices, either alone or in combination.

In some embodiments, the outer porous layer is porous polytetrafluoroethylene (e.g., an ePTFE membrane). In other embodiments, the materials useful as an outer porous layer include biomaterial textiles.

In some embodiments, one or both of the inner layer and the outer layer 210, 220 of the cell encapsulation device is made, primarily or entirely, of a porous material having selective sieving and/or porous properties. The porous material controls the passage of solutes, biochemical substances, viruses, and cells, for example, through the material, primarily on the basis of size. Non-limiting examples of porous materials include, but are not limited to, one or more of the materials set forth above for the inner and outer layers, including biomaterial textiles.

Figure 4:
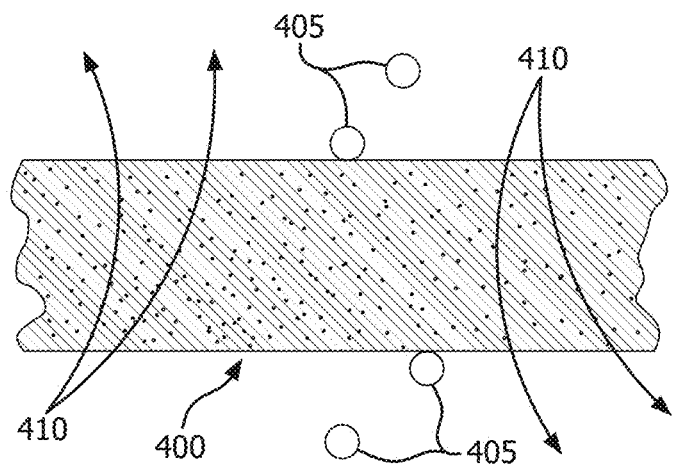
FIGS. 4-10 are schematic illustrations of cross-sections of porous materials used to construct cell encapsulation devices in accordance with embodiments described herein.

In embodiments where the porous material is porous only through a portion of its thickness, the molecular weight cutoff, or sieving property, of the porous membrane begins at the surface. As a result, certain solutes and/or cells do not enter and pass through the porous spaces of the material from one side to the other. FIG. 4 depicts a cross-sectional view of a porous material 400 useful in cell encapsulation devices described herein, where the selective permeability of the porous material 400 excludes cells 405 from migrating or growing into the spaces of the porous material 400 while permitting bi-directional flux of solutes 410 across the thickness of the porous material 400. Vascular endothelial cells can combine to form capillaries thereon. Such capillary formation or neovascularization of the porous material 400 permits fluid and solute flux between tissues of a patient and the contents of cell encapsulation device to be enhanced.

Figure 5:
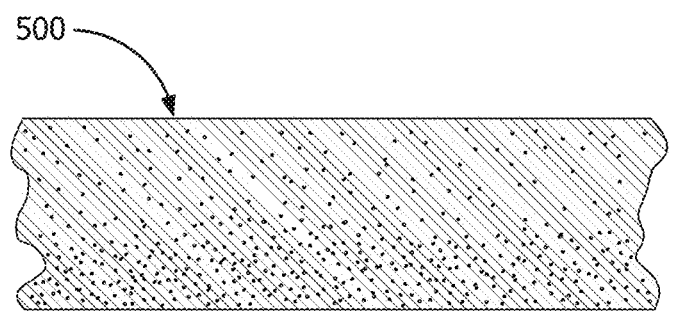
Figure 6:
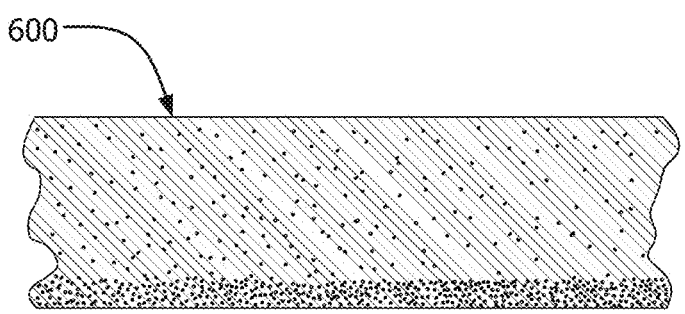

In some embodiments, permeability of the porous material can be varied continuously across the thickness of the porous material of the cell encapsulation devices described herein. As shown in FIG. 5, the selective permeability of the porous material 500 can vary continuously across the thickness of the material as indicated by the gradually increasing density of the stippling in the figure. In some embodiments, the permeability of the porous material 500 is varied from one cross-sectional area of the material to another to form a stratified structure. FIG. 6 is a cross-sectional view of a porous material 600 useful in cell encapsulation devices described herein, where the selective permeability of the porous material 600 varies across the thickness of the porous material 600 as indicated by the increasing density of the stippling in the figure.

Figure 7:
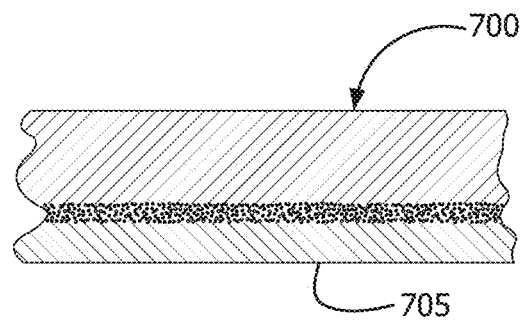

In some embodiments, the permeability of the porous material is varied across its thickness with additional layers of porous material. FIG. 7 is a cross-sectional view of a porous material 700 useful in cell encapsulation devices described herein, where the selective permeability of the porous material 700 is varied across the thickness of the porous material 700 with one or more additional layers of porous material 705. Additional layers of porous material (not illustrated) may have the same composition and permeability as the initial layer of porous material 700 or the one or more additional layers 705 may have a different composition and/or permeability.

Figure 8:
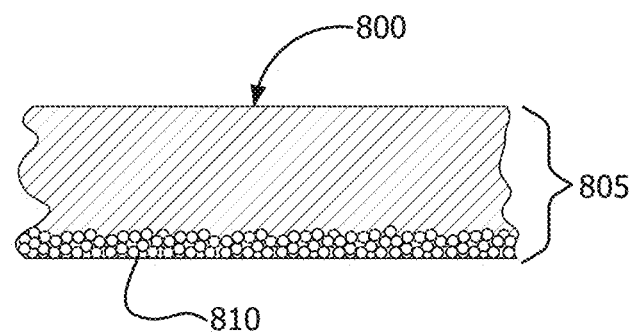

In another embodiment, the selective permeability of the porous material is varied by impregnating the void spaces of the porous material with a hydrogel material. A hydrogel material can be impregnated in all or substantially all of the void spaces of a porous material (e.g., pores of a porous membrane) or in only a portion of the void spaces. For example, by impregnating a porous material with a hydrogel material in a continuous band within the porous material adjacent to and/or along the interior surface of the porous material, the selective permeability of the porous material is varied from an outer cross-sectional area of the porous material to an inner cross-sectional area of the porous material. FIG. 8 is a cross-sectional view of a porous material 800 useful in cell encapsulation devices described herein, where the selective permeability of the porous material 800 is varied across the thickness 805 of the porous material 800 with a hydrogel material 810.

The amount and composition of hydrogel material impregnated into the porous material depends in large part on the particular porous material used to construct an apparatus, the degree of permeability required for a given application, and the biocompatibility of the hydrogel material. Non-limiting examples of useful hydrogel materials for use in the cell encapsulation devices include, but are not limited to, hydrolyzed polyacrylonitrile, alginate, agarose, carrageenan, collagen, gelatin, polyvinyl alcohol, poly(2-hydroxyethyl methacrylate), poly(N-vinyl-2-pyrrolidone), polyethylene glycol, polyethyleneimine, fibrin-thrombin gels, or gellan gum, and copolymers thereof, either alone or in combination. In certain aspects, the total thickness of an porous material (e.g. PTFE)/hydrogel composite may range from about 2 μm to about 1000 μm.

Figure 9:
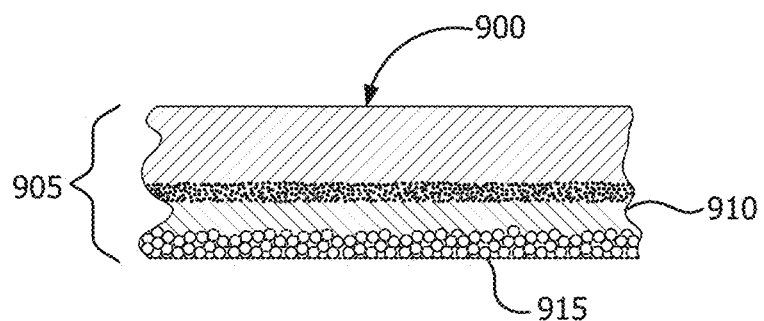

In yet other embodiments, the permeability of the porous material can be varied across the thickness of the porous material with an additional layer of porous material and a further layer of hydrogel material. FIG. 9 is a cross-sectional view of a porous material 900 useful in cell encapsulation devices described herein, where the selective permeability of the porous material 900 is varied across the thickness 905 of the porous material 900 with an additional layer of porous material 910 and a further layer of a hydrogel material 915. One advantage of this embodiment is that this configuration will provide a strong cell and humoral immunoisolation barrier.

Figure 10:
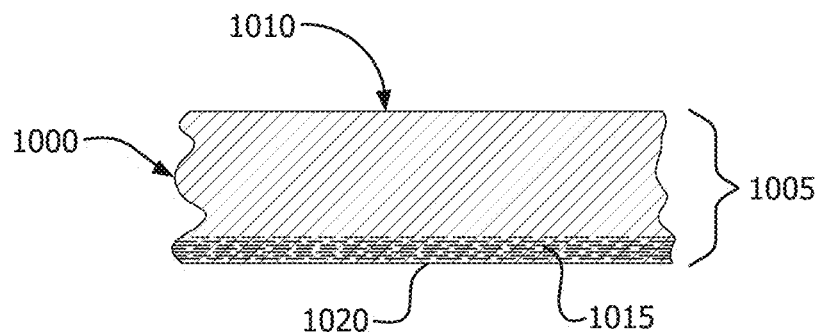

FIG. 10 depicts a cross-sectional view of a porous material 1000 useful in a cell encapsulation devices described herein, where the porous material 1000 includes a cell permeable zone 1005 beginning at the exterior surface 1010 of the polymeric material 1000 and continuing across the thickness of the polymeric material 1000 to a cell exclusion zone 1015 within the polymeric material 1000 adjacent to and continuous with the interior surface 1020 of the polymeric material 1000.

In some embodiments, the structural spacers are formed from a porous material, such as any of the materials described above with respect to the inner and outer layers. In some embodiments, the structural spacers have a porosity that prohibits the ingrowth of cells within the material forming the structural spacers. In some embodiments, the porous material includes porous polytetrafluoroethylene (e.g., expanded polytetrafluoroethylene (ePTFE)), porous polypropylene, porous polyethylene, polyester sulfone (PES), polyurethanes, polyesters, and polyvinylidene fluoride (PVDF), either alone or in any combination.

In an alternative embodiment, the structural spacers are formed from a non-porous material. The non-porous material may include polytetrafluoroethylene (PTFE), polyurethane, polypropylene, polyethylene, polyether amide, polyetheretherketone, polyphenylsulfone, polyslfone, silicone polycarbonate urethane, polyether urethane, polycarbonate urethane, silicone polyether urethane, polyester, polyester terephthalate, melt-processable fluoropolymers, such as, for example, fluorinated ethylene propylene (FEP), tetrafluoroethylene-(perfluoroalkyl) vinyl ether (PFA), an alternating copolymer of ethylene and tetrafluoroethylene (ETFE), a terpolymer of tetrafluoroethylene (TFE), hexafluoropropylene (HFP) and vinylidene fluoride (THV), polyvinylidene fluoride (PVDF), and combinations thereof.

Figure 25:
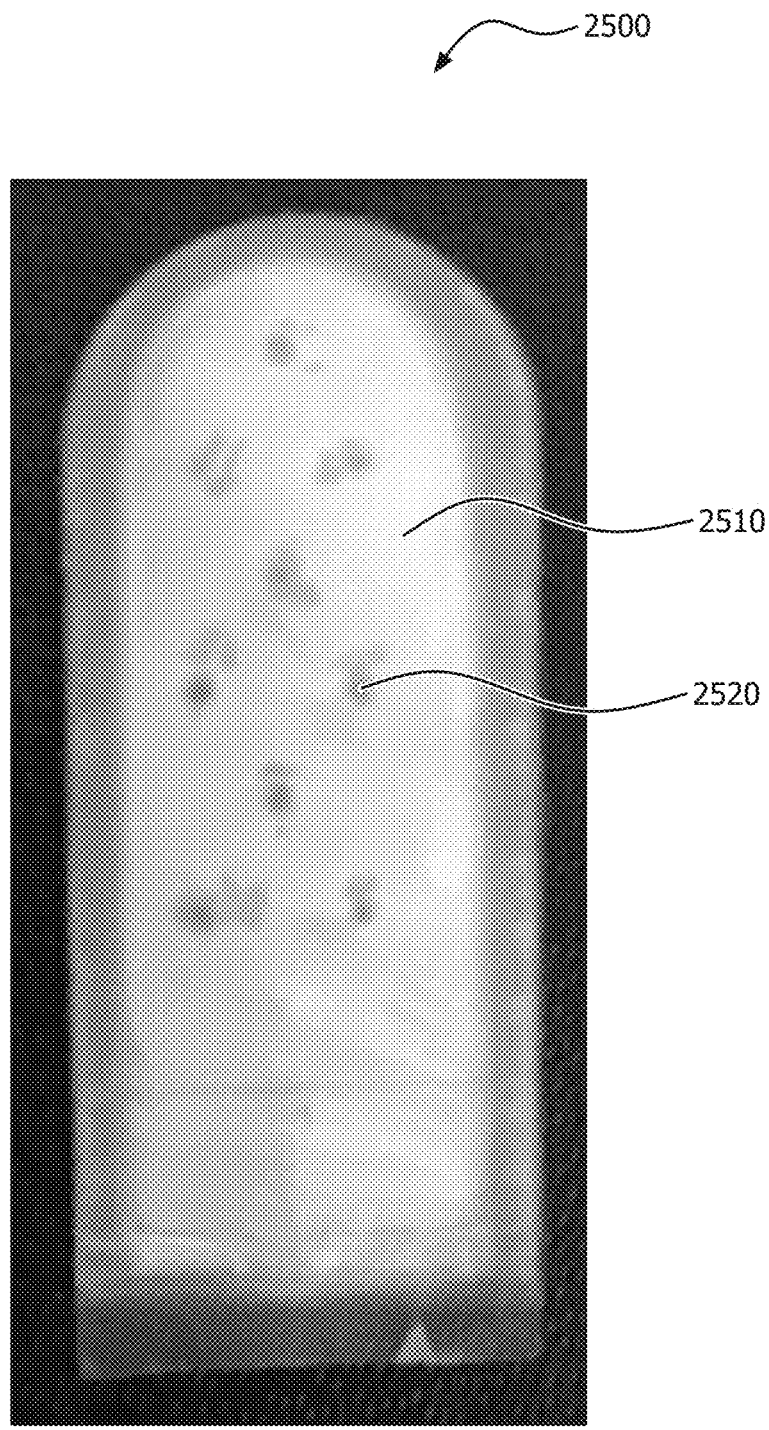
FIG. 25 is a photograph showing the top view of a cell encapsulation device, produced in Example 11 according to embodiments described herein.

In some embodiments, the structural spacers of a cell encapsulation device are adhered to the inner surfaces of one or both of the first and second layers. These structural spacers 2500 may be molded inserts 2510 with three dimensional pillars 2520 such as shown in FIG. 25. The molded inserts 2510 may be positioned between two composite layers in forming a cell encapsulation device. In some embodiments, the structural spacers are adhered to at least one inner porous layer of a composite material. In some embodiments, the first and second layers are both composite materials having inner porous layers, and the structural spacers are adhered to both of the inner porous layers. While the structural spacers penetrate a portion of the pores of the inner porous layers, they do not penetrate the outer porous layer so that the outer porous layer remains undisturbed to allow for cellular ingrowth. In some embodiments, the structural spacers may be formed of or include a shape memory material. Non-limiting examples of useful shape memory materials include shape memory alloys, such as nitinol (nickel-titanium alloy), and shape memory polymers such as polyetheretherketone (PEEK), polymethyl methacrylate, polyethyl methacrylate, polyacrylate, poly-alpha-hydroxy acids, polycaprolactones, polydioxanones, polyesters, polyglycolic acid, polyglycols, polylactides, polyorthoesters, polyphosphates, polyoxaesters, polyphosphoesters, polyphosphonates, polysaccharides, polytyrosine carbonates, polyurethanes, polyurethanes with ionic or mesogenic components made by a pre-polymer method, and copolymers or polymer blends thereof. Other block copolymers also show the shape-memory effect, such as, for example, a block copolymer of polyethylene terephthalate (PET) and polyethyleneoxide (PEO), block copolymers containing polystyrene and poly(1,4-butadiene), and an ABA triblock copolymer made from poly(2-methyl-2-oxazoline) and polytetrahydrofuran. Non-limiting shape memory alloys include, but are not limited to, copper-aluminum-nickel, copper-zinc-aluminum, and iron-manganese-silicon alloys.

Figure 11:
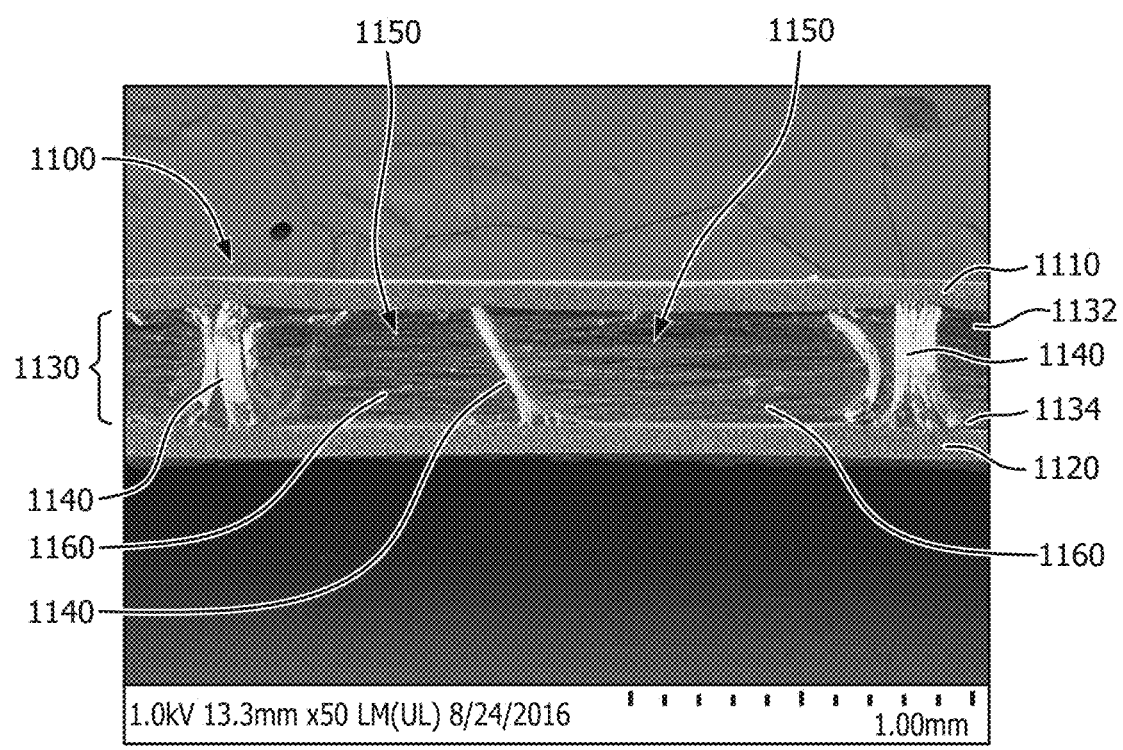
FIG. 11 is a scanning electron microscope (SEM) image of a cross-section of a membrane having polytetrafluoroethylene (PTFE) structural elements for use in a cell encapsulation device according to embodiments described herein.
Figure 12:
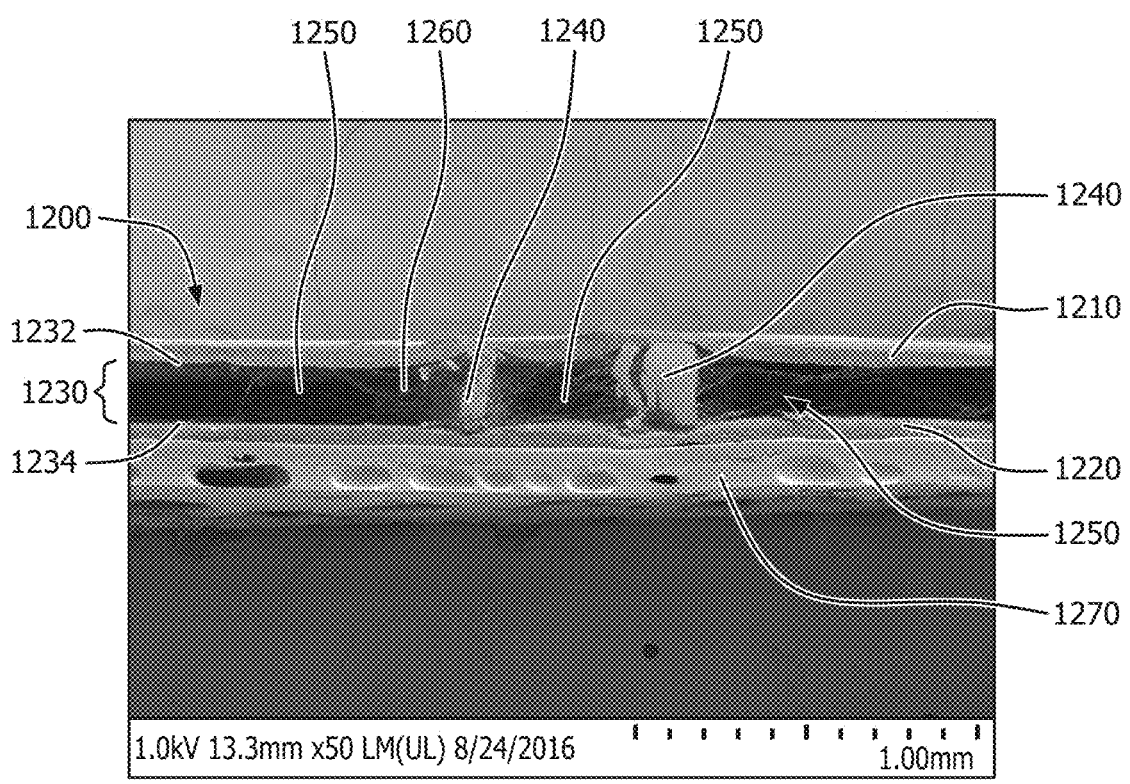
FIG. 12 is a scanning electron microscope (SEM) image of a partial cross-section of a membrane having polytetrafluoroethylene (PTFE) structural elements for use in a cell encapsulation device according to embodiments described herein.

In some embodiments, the structural spaces are formed of polytetrafluoroethylene (PTFE), such as are depicted in FIGS. 11 and 12. FIG. 11 is a scanning electron micrograph (SEM) of a cross-section of a PTFE membrane 1100 that may be used in a cell encapsulation device according to embodiments described herein. The membrane of FIG. 11 includes first and second layers 1110, 1120 that are cell retentive layers (also called tight layers), a chamber 1130 positioned between the first and second layers 1110, 1120, first and second interior surfaces 1132, 1134 in the chamber 1130 that are spaced apart from each other by the PTFE structural spacers 1140, and reservoir spaces 1150 to receive cells (not shown). The structural spacers 1140 within the chamber 1130 maintain the distance between the first and second interior surfaces 1132, 1134. Fibrils 1160 are visible as the thin, horizontal lines inside the chamber 1130.

FIG. 12 is an SEM of a cross-section of another PTFE membrane 1200 that may be used in a cell encapsulation device according to embodiments described herein. The membrane shown in FIG. 12 includes first and second layers 1210, 1220 that are cell retentive layers (also called tight layers), a chamber 1240 located between the first and second layers 1210, 1220, first and second interior surfaces 1232, 1234 spaced apart from each other, PTFE structural spacers 1240 positioned within the chamber 1230 to maintain the distance between the first and second interior surfaces 1232, 1234, and reservoir spaces 1250 to receive cells (not shown). Fibrils 1260 are visible as thin, horizontal lines inside the chamber 1230. The element labeled 1270 is adhesive tape used to prepare the PTFE membrane 1200, but which is removed prior to use and is not part of this or any other embodiment.

Figure 13:
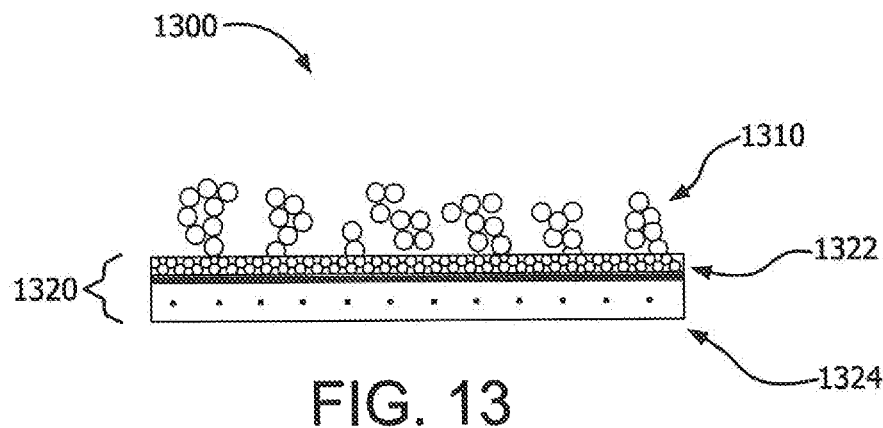
FIG. 13 is a schematic illustration of structural spacing elements formed by powder coating a thermoplastic polymer onto the surface of a cell retentive layer according to embodiments described herein.
Figure 16A:
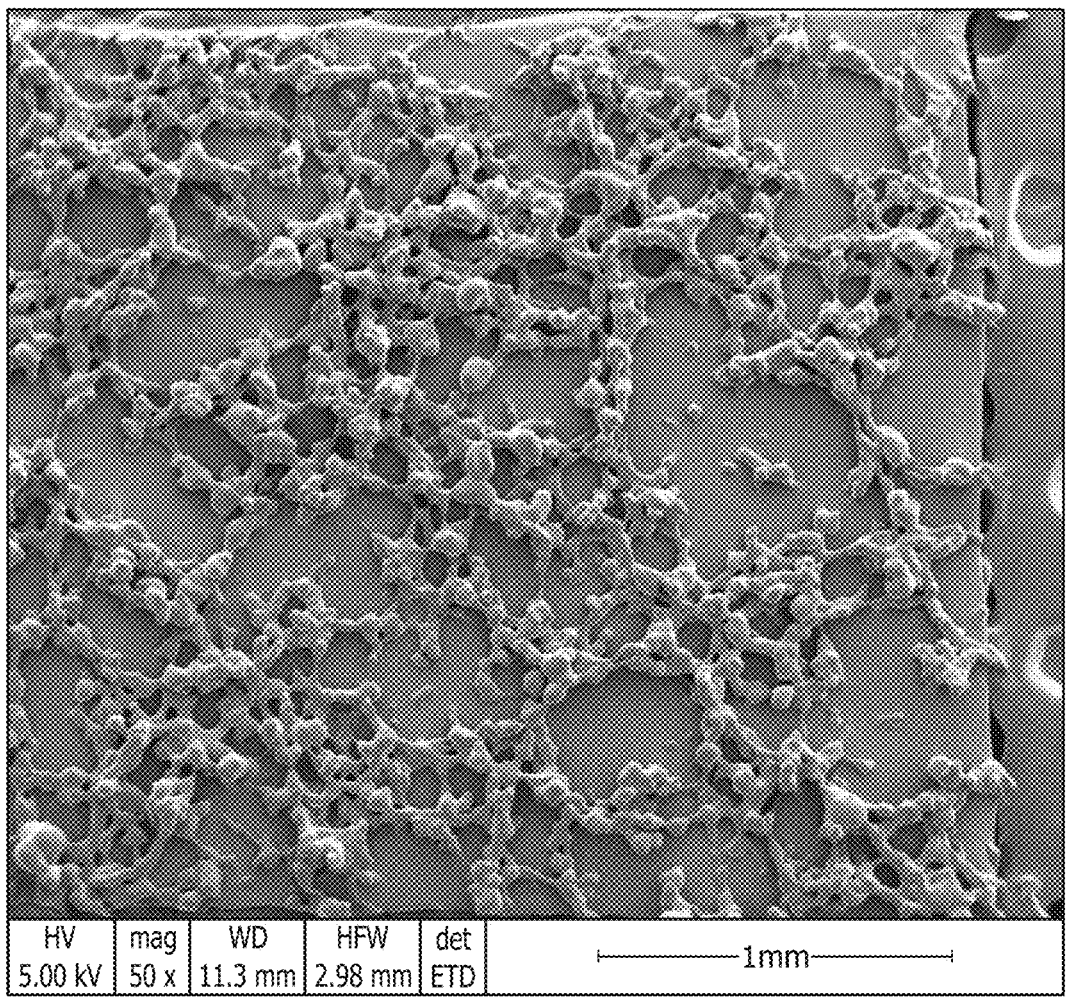
FIG. 16A is a scanning electron micrograph (SEM) of the top surface of a PTFE membrane powder coated with fluorinated ethylene propylene at 50× magnification according to embodiments described herein.
Figure 16B:
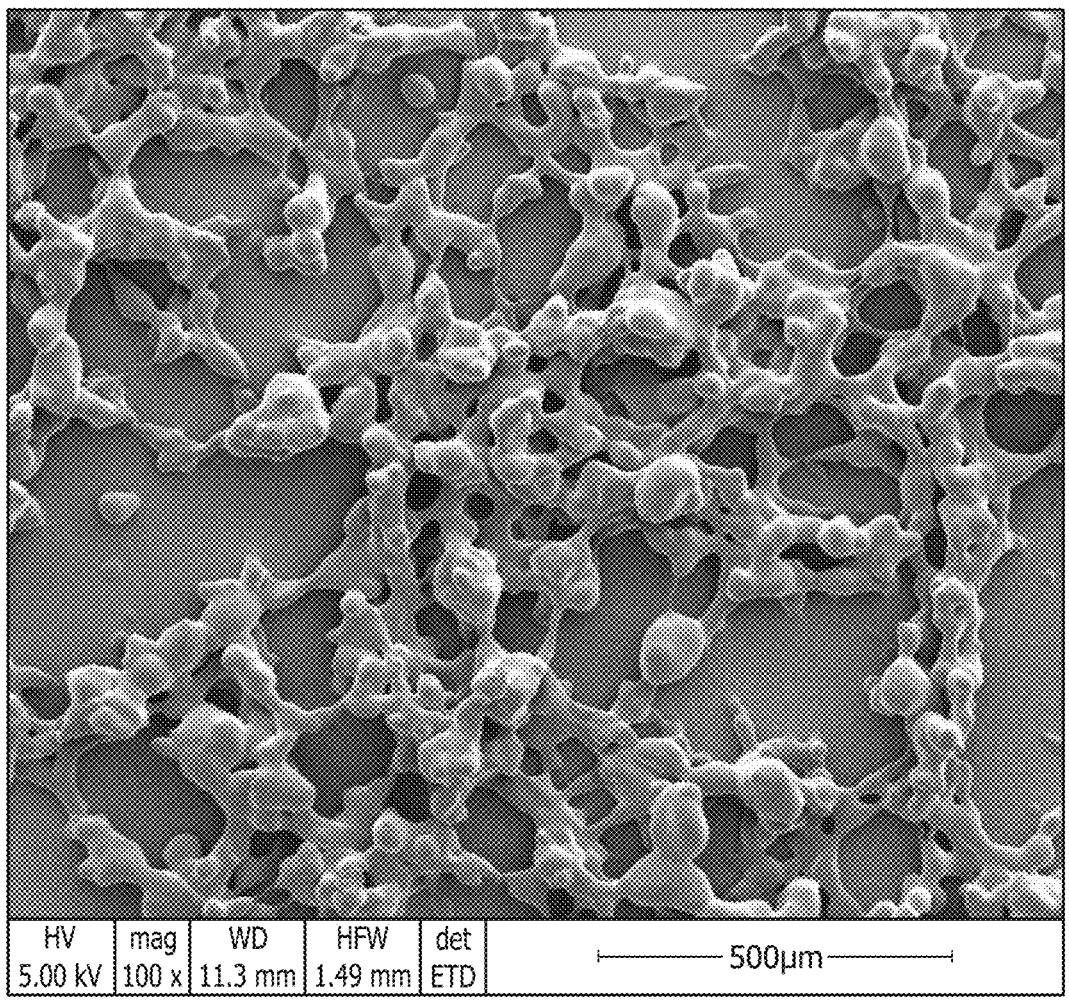
FIG. 16B is a scanning electron micrograph (SEM) of the top surface of a PTFE membrane powder coated with fluorinated ethylene propylene at 100× magnification according to embodiments described herein.

In some embodiments, the structural spacers may be formed by powder coating a fluoropolymer powder onto a cell retentive layer to form at least a part of a structural spacer. Part of a structural spacer is referred to herein as a structural spacing element 1300 in FIG. 13. FIG. 13 is a schematic illustration of a fluoropolymer powder 1310 deposited on a composite layer 1320 that includes a cell retentive layer 1322 and a cell vascularizing layer 1324. FIGS. 16A and 16B are scanning electron micrographs (SEM) of the top surface of a polytetrafluoroethylene membrane that has been powder-coated with fluorinated ethylene propylene (FEP) taken at 50× magnification and 100× magnification, respectively.

Figure 14:
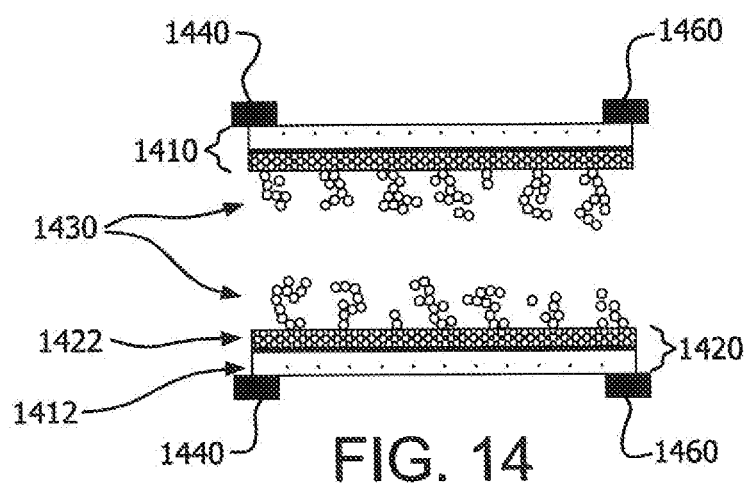
FIG. 14 is a schematic illustration depicting the orientation of a top composite layer, a bottom composite layer, and fluoropolymer spacing elements aligning to form structural spacers within a cell encapsulation device according to embodiments described herein.

To form a chamber of a cell encapsulating device as described herein, two composite cell retentive layers, two single cell retentive layers, or a combination of a composite cell retentive layer and a single cell retentive layer having a thermoplastic polymer powder coated thereon may be sandwiched together such that at least some of the polymeric structural spacing elements align to form structural spacers that connect the two layers. FIG. 14 depicts the orientation of a top composite layer 1410, a bottom composite layer 1420, and fluoropolymer spacing elements 1430 that align to form structural spacers within a cell encapsulation device. FIG. 14 further shows two outer vascularizing layers 1412, two inner cell retentive layers 1422, having the fluoropolymer powder structural spacing elements 1430 thereon, perimeter sealing rings 1440, 1460 which are used to seal the two composite layers 1410, 1420 around their perimeter. In some embodiments, the perimeter sealing rings 1440, 1460 are internally positioned within the device (not illustrated).

Figure 15:
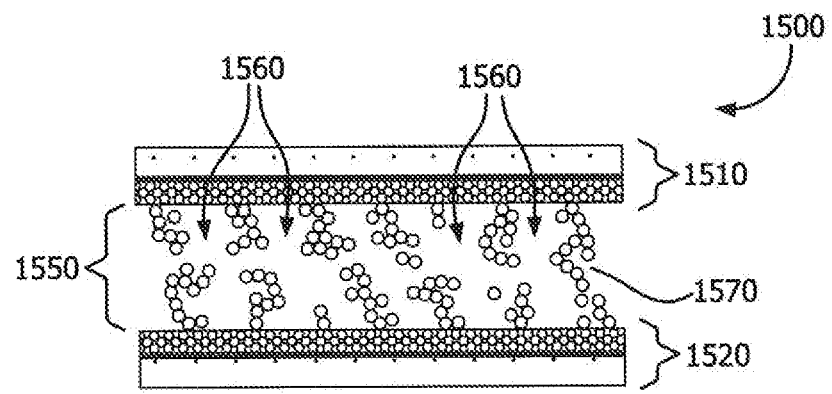
FIG. 15 is a schematic illustration of a cross-sectional view of the cell encapsulation device formed with the materials shown in FIG. 14 according to embodiments described herein.

FIG. 15 is a cross-sectional view of the cell encapsulation device formed with the materials shown in FIG. 14. The cell encapsulation device 1500 includes two composite layers 1510, 1520 and structural spacers 1570 extending between the two composite layers 1510, 1520 to maintain a distance 1550 between the two composite layers 1510, 1520. FIG. 15 shows at least some of the fluoropolymer powder structural elements aligning to form structural spacers 1570 that maintain a distance 1550 between the two composite layers 1510, 1520 and form reservoir spaces 1560 for the retention of cells. A port (not illustrated) is positioned in fluid communication with reservoir spaces 1560 between the two composite layers 1510, 1520 for the insertion of cells into the reservoir spaces 1560.

Figure 17:
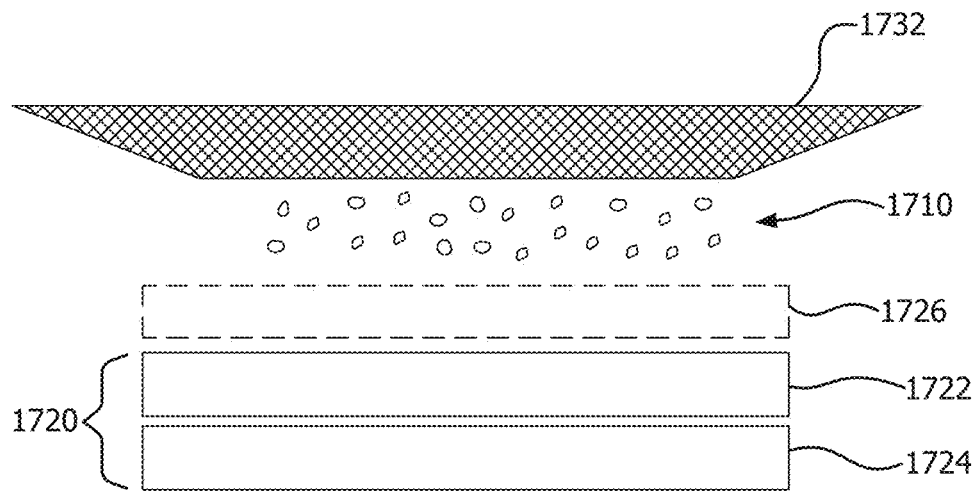
FIG. 17 is a schematic illustration of the selective deposition of a thermoplastic polymer onto a cell retentive layer according to embodiments described herein.
Figure 17A:
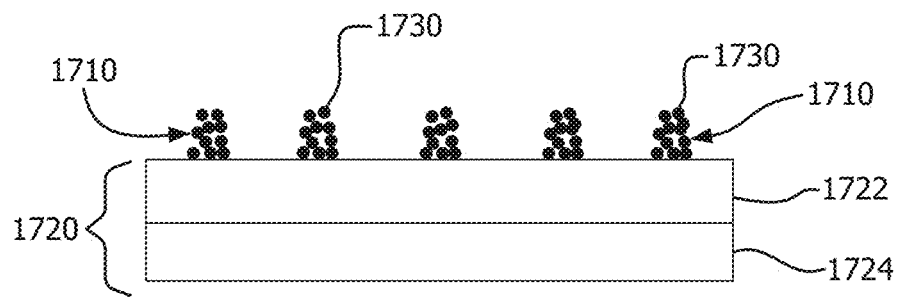
FIG. 17A is a schematic illustration of structural spacing elements formed by the selective deposition of a thermoplastic polymer powder onto a cell retentive layer according to embodiments described herein.

In another embodiment, the structural spacers of the cell encapsulation device may be formed by applying a thermoplastic polymer powder onto a desired or specific location on a cell retentive layer to form at least a part of a structural spacer. FIG. 17 is a schematic illustration of a thermoplastic polymer powder 1710 being deposited through a sifter element 1732 onto a composite layer 1720 that includes a cell retentive layer 1722 and a cell vascularizing layer 1724. By positioning a removable patterned mask 1726 (or other similar patterning device) on the cell retentive layer 1722, the thermoplastic polymer powder 1710 is uniformly or substantially uniformly applied onto the cell retentive layer 1722 in the desired locations and/or in a desired pattern. FIG. 17A illustrates the final lay down of the thermoplastic polymer powder 1710 into structural spacing elements 1730.

Figure 17B:
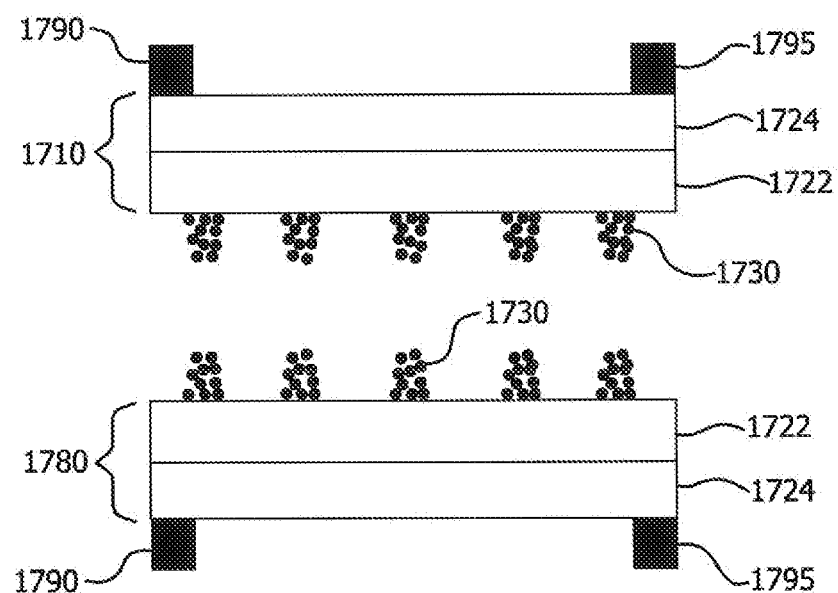
FIG. 17B is a schematic illustration of the orientation of the components forming a cell encapsulation device utilizing selective deposition of a thermoplastic polymer powder onto a cell retentive layer according to embodiments described herein.

FIG. 17B depicts the orientation of a top composite layer 1710, a bottom composite layer 1780, thermoplastic spacing elements 1730 that align to form structural spacers in a cell encapsulation device. FIG. 17B further shows two outer vascularizing layers 1724, two inner cell retentive layers 1722 having the thermoplastic structural elements 1730 thereon, and perimeter sealing rings 1790, 1795 which are used to seal the two composite layers around their perimeter.

Figure 17C:
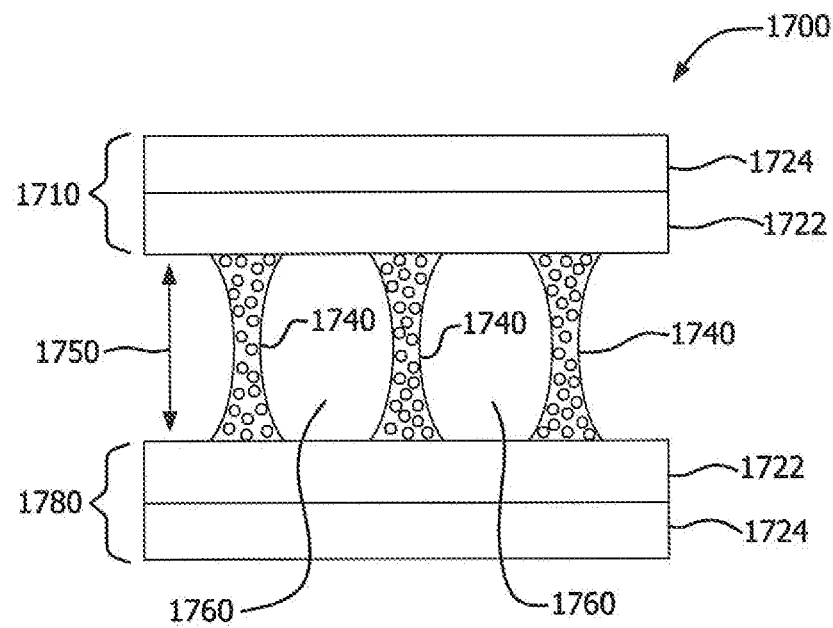
FIG. 17C is a schematic illustration of a cell encapsulation device with structural spacers formed by the thermoplastic powder according to embodiments described herein.

FIG. 17C is a cross-sectional view of the cell encapsulation device formed with the materials shown in FIG. 17B. The cell encapsulation device 1700 includes two composite layers 1710, 1780 and structural spacers 1730 extending between the two composite layers 1710, 1780 to maintain a distance 1750 between the two composite layers 1710, 1780. FIG. 16C depicts the fluoropolymer powder structural elements aligning to form structural spacers 1740 that maintain the distance 1650 between the two composite layers 1710, 1780 and form reservoir spaces 1760 for the retention of cells. In some embodiments, the thermoplastic structural elements 1730 do not have to align to form a structural spacer 1740, rather, the structural spacer 1740 may be formed as a structural spacer 1740 from one side and the composite layer and be attached to the opposing composite layer. A port (not illustrated) is positioned in fluid communication with reservoir spaces 1760 between the two composite layers 1610, 1680 for the insertion of cells into the reservoir spaces 1760.

Figure 18:
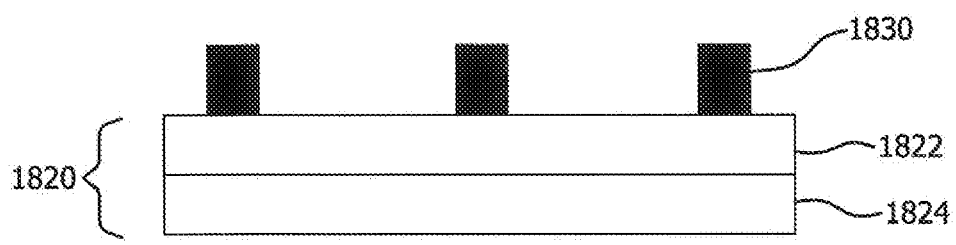
FIG. 18 is a schematic illustration of a structural spacing element formed by selectively laying down a thermoplastic polymer onto a cell retentive layer according to embodiments described herein.

In yet another embodiment, the structural spacers of the cell encapsulation device may be formed by printing (or otherwise laying down) a thermoplastic polymer onto a cell retentive layer to form at least a part of a structural spacer. Any conventional printing technique such as transfer coating, screen printing, gravure printing, ink-jet printing, 3D printing, patterned imbibing, fused filament fabrication, fused deposition modeling, stereolithography, photopolymerization, selective laser sintering, and knife coating may be utilized to place a thermoplastic polymer onto the cell retentive layer. FIG. 18 illustrates a thermoplastic polymer in the form of structural spacing elements 1830 positioned on a composite layer 1820 that includes a cell retentive layer 1822 and a cell vascularizing layer 1824 (after printing is complete).

FIG. 18A depicts the orientation of a top composite layer 1870, a bottom composite layer 1880, thermoplastic spacing elements 1830 that align to form structural spacers for a cell encapsulation device. FIG. 18A further shows two outer vascularizing layers 1824, two inner cell retentive layers 1822 having the thermoplastic structural elements 1830 thereon, perimeter sealing rings 1890, 1895 which seal the two composite layers 1870, 1880 around their perimeter. In some embodiments, the perimeter sealing rings 1890, 1895 are internally positioned within the device (not illustrated).

FIG. 18B is a cross-sectional view of the cell encapsulation device formed with the materials shown in FIG. 18A. The cell encapsulation device 1800 includes two composite layers 1870, 1880 and structural spacers 1840 extending between the two composite layers 1870, 1880 to maintain a distance 1850 between the two composite layers 1870, 1880. FIG. 18B depicts the polymeric structural elements aligning to form structural spacers 1840 that maintain the distance 1850 between the two composite layers 1870, 1880 and form reservoir spaces 1860 for the retention of cells. In some embodiments, the structural spacing elements need not align, but are printed so at to touch the composite layer opposing the structural spacing element. A port (not illustrated) is positioned in fluid communication with reservoir spaces 1860 between the two composite layers 1870, 1880 for the insertion of cells into the reservoir spaces 1860.

Figure 19:
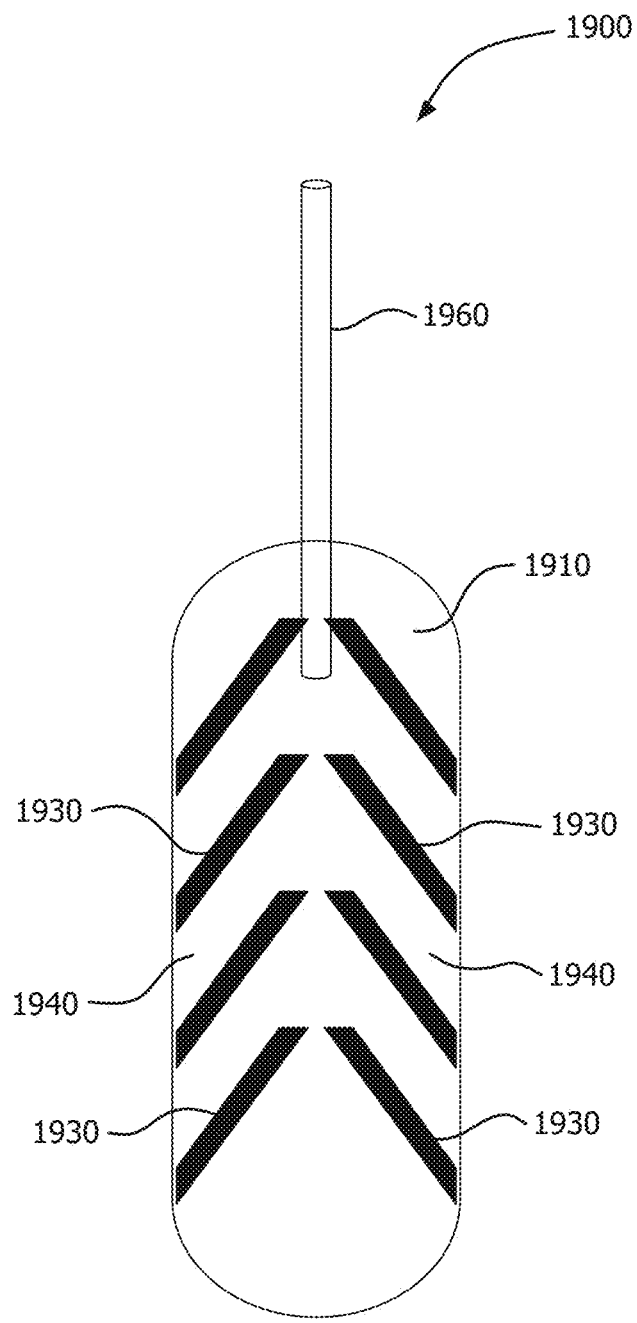
FIG. 19 is a cross-section of structural supports formed in an exemplary pattern for use in a cell encapsulation device according to embodiments described herein.
Figure 20:
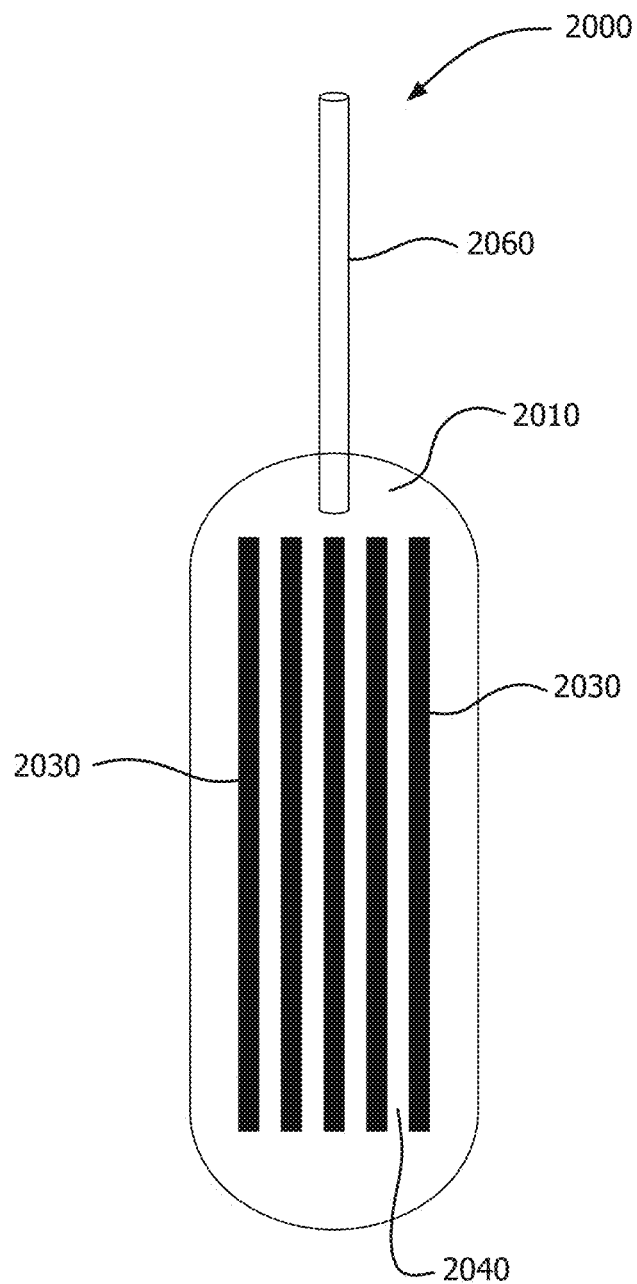
FIG. 20 is a cross-section of structural supports formed in another exemplary pattern for use in a cell encapsulation device according to embodiments described herein.

It is to be appreciated that any number of patterns or geometries may be printed or otherwise applied to the composite layers to form the structural elements and/or the structural spacers, such as, for example, dots, straight lines, angled lines, curved lines, dotted lines, grids, etc. The patterns or geometries may be designed, for example, to accommodate specific cell spacing, therapeutic requirements, flow patterns and pressure, and/or mechanical strength. Non-limiting examples of patterns for use in the cell encapsulation devices are shown schematically in FIGS. 19 and 20. The structural supports 1930, 2030 are located within chambers 1910, 2010 and define reservoir spaces 1940, 2040 interconnected by channels formed by and among the structural supports 1930, 2030. Ports 1960 and 2060 are in fluid communication with the chambers 1910, 1910 of the cell encapsulation device 1900, 2000. The patterns are not particularly limited so long as the reservoir spaces located within and/or between the structural supports are in fluid communication with the port.

The structural spacers enable the use of more flexible outer layers of the cell encapsulation device because they provide support within the cell encapsulation device to maintain a generally planar structure or shape (vs. stiff, bulky materials located on the outside of conventional devices). The structural supports also allow for optimizing or tailoring the bulk device stiffness through the specific design and/or geometry of the patterns of the structural spacers within the cell encapsulation device. The terms "flexible" and "flexibility" as used herein, are meant to describe overall compliance or bending stiffness of the cell encapsulation device and compliance of the host interface/ingrowth layers in contact with the host tissue, such that those ingrowth layers match the compliance of the host tissue as well as the compliance of the cell encapsulation device relative to the host tissue such that the cell encapsulation device can flex and move with the host tissue without an excessive inflammatory response due to a significant mismatch in the compliance of the device and host interface/ingrowth layers with the host tissue.

The structural spacers separate the first and second layers such that there is a distance between the layers. The structural spacers maintain that distance under an applied force. The applied force may be an external compressive force that would tend to cause the chamber between the first and second layers to collapse in the absence of the structural spacers. For example, the surrounding tissue may exert a compressive force on the device in vivo, or a clinician may exert a compressive force on the outside of the device prior to or during insertion. If the external compressive force decreases the distance between the first and second interior surfaces, cells within the encapsulation device may be subjected to undesirable mechanical stimuli which could result in minimized cell functionality or cell fatality. In some embodiments, the cell encapsulation devices are intended for subcutaneous implantation, and thus the compressive force may be caused by contact with a patient while the device is implanted in the patient, such as by giving the patient a hug or a pat on the back, or if the patient falls.

Alternatively, the applied force may be an internal expansive force that would tend to cause the chamber between the first and second layers to expand to a rounded, balloon-like membrane in the absence of the structural spacers. For example, pressure may be required to inject a plurality of cells into the chamber. In one example, pressure can be caused by over-inflation at the time of insertion, e.g., due to operator error. In another example, pressure can be caused by an increase of cells due to cellular propagation and multiplication.

In some embodiments, a cell encapsulation device described herein includes first and second interior surfaces that each independently have a surface area. The surface area of the first and second interior surfaces may vary depending on the size of the cells or other biological moieties and/or the implantation site and/or on the average distance between the first and second interior surfaces. The surface area will further depend on the specific cell therapy employed and the productivity of the cells required to meet the therapeutic need. In some examples, the average distance between the first and second interior surfaces In some examples the distance between the first and second interior surfaces is at least about 50 microns (e.g., between 50 microns and 100 microns), at least 100 microns (e.g. between 100 and 150 microns), at least 150 microns (e.g., between 150 microns and 200 microns, or at least 200 microns (e.g. between 200 microns and 250 microns). In some examples, the average distance may be about 50 microns, 100 microns, 200 microns, 250 microns, at least 250 microns, or 500 microns or more. As used herein, the phrase "maintaining an average distance" means that the distance between the first composite layer (or first interior surface) and second composite layer (or second interior surface) in a chamber are separated by a distance on average that is at least about 50 microns throughout at least one dimension of the cell encapsulation device where cell reside, such as, for example, the length and/or width (or first and second diameter) in the chamber of the cell encapsulation device and which is substantially consistent in thickness across that dimension. In one embodiment maintaining the average distance may place the first layer in a substantially parallel relationship with the second layer along at least one dimension of chamber, e.g., along the length and/or the width (or first and second diameter) of the chamber. In other words, the structural spacers maintain the thickness of the cell encapsulation device within the chamber in cross-section. Also, the structural spacers permit the use of a more flexible material(s), such as PTFE, on the outside of the device. Additionally, the structural spacers provides sufficient strength for the cell encapsulation device to survive mechanical forces over time in vivo as well as to maintain the average thickness. It is important that the materials used in the composite layer, for example ePTFE, also have sufficient tensile strength to maintain the integrity of the cell encapsulation device both during implant and in vivo.

In some embodiments, the structural spacers utilized in the cell encapsulation devices described herein are designed to minimize the footprint (base) of the spacer on the underlying material (e.g., cell isolation membrane) which in turn maximizes the effective area for nutrients, biomolecules, and therapeutic exchange. Some embodiments have a height to base aspect ratio from 1/5 to 10/1. In some embodiments, the height to base ratio may be 1/3 or 1/1 or 2/1 or greater. In some cases the aspect ratio can be high such that the height is greater than the base to minimize footprint while preserving the average distance within the chamber. In other cases the aspect ratio be lower such that the base is greater than the height to maintain strength and buckling resistance. This is a tradeoff that can be balanced through the specific design and geometries of the structural supports. The footprint of the structural spacers is small in comparison to the internal surface area of the cell encapsulation device. This small footprint also allows for greater internal volume within the cell encapsulation device and easier access for cell insertion into the cell reservoirs. In addition, a smaller footprint results in greater flexibility (e.g., it is less stiff) compared to a device that has a larger footprint (e.g., a weld). Additionally, and unlike welding, the microporous structure above the structural spacers is maintained. This permits host tissue attachment (e.g., cells, capillaries, vascularization structures, etc.) above the structural spacers because that space above the structural spacers is porous. In embodiments where the structural spacers are porous, they are able to permit nutrient and biomolecule passage while also maintaining the average distance. In addition, the general structure of the structural spacer increases the overall surface area within the chamber.

In some embodiments, the chamber comprises structural spacers covering at least a portion of the surface area of each of the first and second interior surfaces. In some embodiments, the structural spacers cover at least 2% of the first and second interior surfaces, at least about 5% of the first and second interior surfaces, about 5% of the first and second interior surfaces, from about 5% to about 50% of the first and second interior surfaces, from about 5% to about 70% of the first and second interior surfaces, or no more than about 5% of the first and second interior surfaces, or no more than about 2% of the first and second interior surfaces. In some embodiments, the structural spacers divide the chamber into at least two reservoir spaces. Boundaries of the reservoir spaces are defined by the sealed periphery, structural spacers, and the planar regions between the structural spacers or between the structural spacers and the sealed periphery. The number of reservoir spaces is not particularly limited and the chamber may contain up to 100,000 or more reservoir spaces.

In some embodiments, at least two reservoir spaces are interconnected by channels formed by and among the structural supports. The interconnection between the reservoir spaces permits the flow of cells into each of the reservoirs from a single port. The reservoir spaces permit the insertion of cells without expanding or varying the average thickness between the inner and outer composite layers. It is to be appreciated, however, that even though the average thickness remains constant, there may be localized regions of increased pressure that cause a temporary increased localized thickness between structural spacers without significantly changing the average thickness. For instance, the geometry and spacing of the structural supports can be adjusted to tailor the localized increase in distance (or deflection) between the structural supports.

In addition, the reservoir spaces may take numerous configurations, and may be in the form of lanes (where the structural spacers are aligned parallel to each other), a geometric shape (where the structural spacers are spaced to form generally planar structure or shape, e.g. in the general form of a rectangle, circle, square, semi-circle, semi-oval, etc.). In other embodiments, the at least two reservoir spaces are discrete (i.e., are not fluidly connected). Each discrete reservoir space may have a separate port. In other embodiments, a portion of the reservoir space may be interconnected and another portion may be discrete (not connected).

In some embodiments, the cell encapsulation devices may be formed from a single material or membrane having regions of varying porosity, including at least a first layer, an open cell region adjacent to the first layer, and a second layer adjacent to an opposing side of the open cell region, where the material is sealed around a periphery such that the open cell region becomes a chamber within the material. The chamber is bound by the first layer, the second layer and the seal. In some embodiments, the membrane may be sealed around its periphery. In other embodiments, a section of the membrane may be sealed and then portions of the membrane outside of the seal may be trimmed to create the device with a sealed periphery.

Figure 21A:
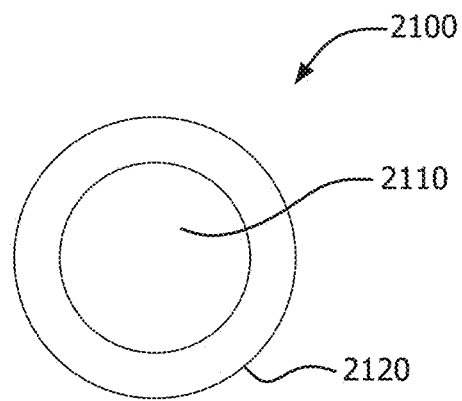
FIG. 21A is a cross-section of a bicomponent fiber used to form structural spacers in a cell encapsulation device according to embodiments described herein.
Figure 21B:
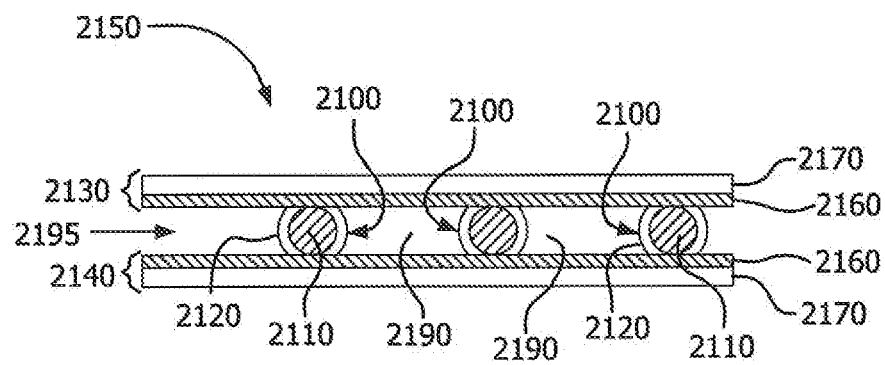
FIG. 21B is a cross-section of a cell encapsulation device formed using bicomponent fibers according to embodiments described herein.

In another embodiment, the structural spacers may take the form of a fiber or fibers. As one non-limiting example, a bicomponent fiber may be used to form a spacer. FIG. 21A schematically depicts a bicomponent fiber 2100 having an inner core 2110 and an outer sheath 2120 where the outer sheath 2120 has a lower melting temperature than the melting temperature of the material forming the inner core 2110. The outer sheath 2120 may be formed of a polymeric material that, when heated to a temperature above its melting temperature, melts and acts as an adhesive. FIG. 21B is a schematic illustration of a cross-section of a cell encapsulation device 2150 that includes a bicomponent fiber 2100, a first composite layer 2130 and a second composite layer 2140. The first and second composite layers 2130, 2140 each contain a cell retentive layer 2160 and a cell vascularizing layer 2170.

The bicomponent fibers 2100 may be positioned in a desired pattern on the cell retentive layer 2160 of the composite layer 2140. The second composite layer 2130 is then positioned on the bicomponent fibers 2100 such that the cell retentive layer 2160 is facing the bicomponent fibers 2100. Upon the application of heat sufficient to at least partially melt the material forming the outer sheath 2120 of the bicomponent fiber 2100 (but not the inner core material 2110), the material of the outer sheath melts and/or becomes sufficiently sticky to adhere core 2110 of the bicomponent fibers 2100 to the composite layers 2130, 2140. Reservoir spaces 2190 are defined between the core 2110 fibers. A combination of heat and pressure may be applied to the outer edges of the composite layers 2130, 2140 to form a sealed periphery (not illustrated). In addition, a port (not depicted) extends through the sealed periphery such that it is in fluid communication with the chamber 2195.

Figure 22:
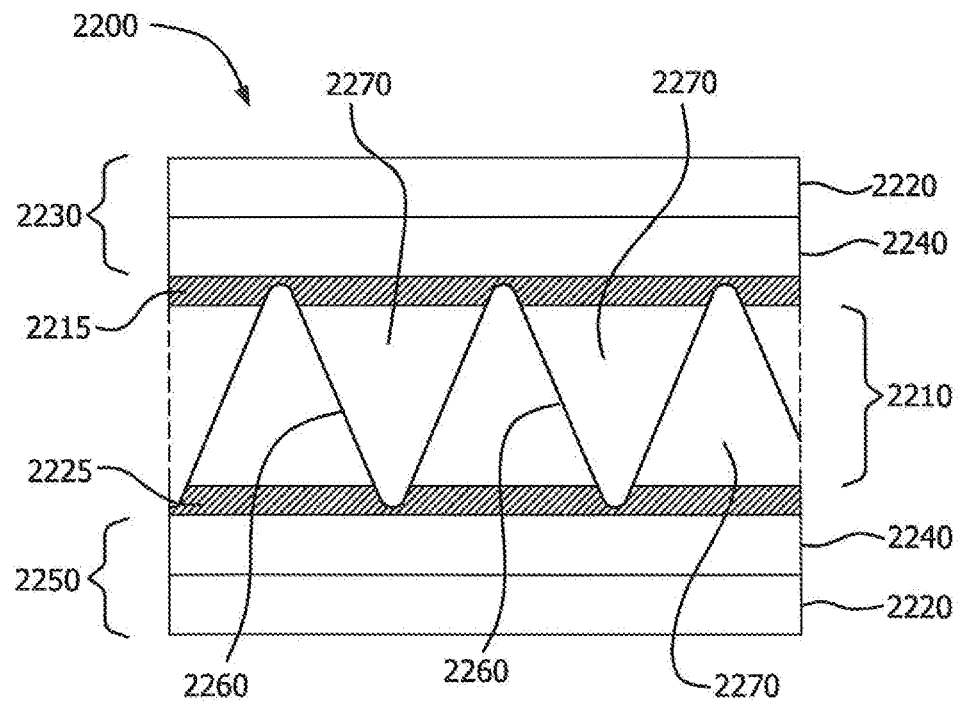
FIG. 22 is a cross-section of a cell encapsulation device formed using a three-dimensional woven structure according to embodiments described herein.

In another embodiment, a three dimensional woven structure that includes an internal structural restraint may be used to form a cell encapsulation device. Such a woven cloth structure is commercially available from Secant Medial, Telford, Pa. FIG. 22 is a schematic illustration of a cell encapsulation device 2200 formed with a three dimensional woven structure. As shown, the woven material 2210 includes structural restraints 2260 between a first side 2215 of the woven material 2210 and a second side 2225 of the woven material 2210 that resist compression and assist in maintaining the thickness of the three dimensional woven material, yet still provide a soft and compliant device. When the woven material 2210 is sandwiched between a first composite layer 2230 and a second composite layer 2250, reservoirs 2270 are formed. As with other embodiments described herein, the first and second composite layers 2230, 2250 each include a cell retentive layer 2240 and a vascularizing layer 2220. The edges of the cell encapsulation device 2200 may be fused by heat sealing the woven material (not depicted). Alternatively, the edges may be filled with a liquid silicone rubber (and subsequently cross-linked) or melt processable thermoplastic to form a sealed structure. In addition, a port (not depicted) extends through the sealed periphery such that it is in fluid communication with the reservoirs 2270.

In a further embodiment, a structural spacer may be formed by printing a thermoplastic polymer bead, such as fluorinated ethylene propylene (FEP) or a thermoplastic terpolymer of tetrafluoroethylene (TFE), hexafluoropropylene (HFP), and vinylidine fluoride (VDF), onto a cell retentive layer, such as with a 3D printer. It is to be appreciated that the thermoplastic polymer is not restricted to fluoropolymers, and can be adapted in a straightforward manner to any melt processable polymer, such as, for example, a hydrocarbon polymer. Additionally, one of skill in the art would appreciate that other techniques are known for achieving a desired structure of patterned polymer dots or lanes arranged in a pattern. These techniques include, but are not limited to, gravure printing, mask (or screen) printing (such as discussed above), direct polymerization, laser fusing of a powder, fused filament fabrication, and other techniques commonly used in 3D printing of polymer structures. Additionally, a "pull-away" technique can be used to print a dot of material and quickly move the nozzle away in the Z-axis. This rapid movement will allow a thin tapered strand to be left rising up from the dot. Once all dots are printed, the strand may be shaved to the appropriate height by blade, laser or other known cutting methods.

The thermoplastic polymer bead may be placed onto the cell retentive layer in any pattern, such as, but not limited to, dots, straight lines, angled lines, curved lines, dotted lines, grids, and combinations thereof. A bead (or multiple beads) may also be used to form a perimeter seal. A second cell retentive layer may be positioned on the polymer beads. It is to be appreciated that the cell retentive layers may be part of a composite layer as discussed herein. Heat and pressure may be applied to at least partially melt the thermoplastic bead(s) and bond the two cell retentive layers to each other. The pre-determined pattern printed by the 3D printer forms reservoirs for the placement of cells therein. In addition, a nitinol wire (or other shape memory material such as described above) may be positioned in between the beads, such as when they are used to form a perimeter seal, to provide additional stiffness to the cell encapsulation device. Nitinol (nickel-titanium alloy) wire (or other shape memory materials, alloys, or polymers such as described above may alternatively be used to form structural spacers. In one embodiment, a fluorothermoplastic sheet may be used to seal the edges and form a sealed periphery. A port may extend through the sealed periphery to provide an access for the introduction of the cells into the reservoirs.

Figure 23:
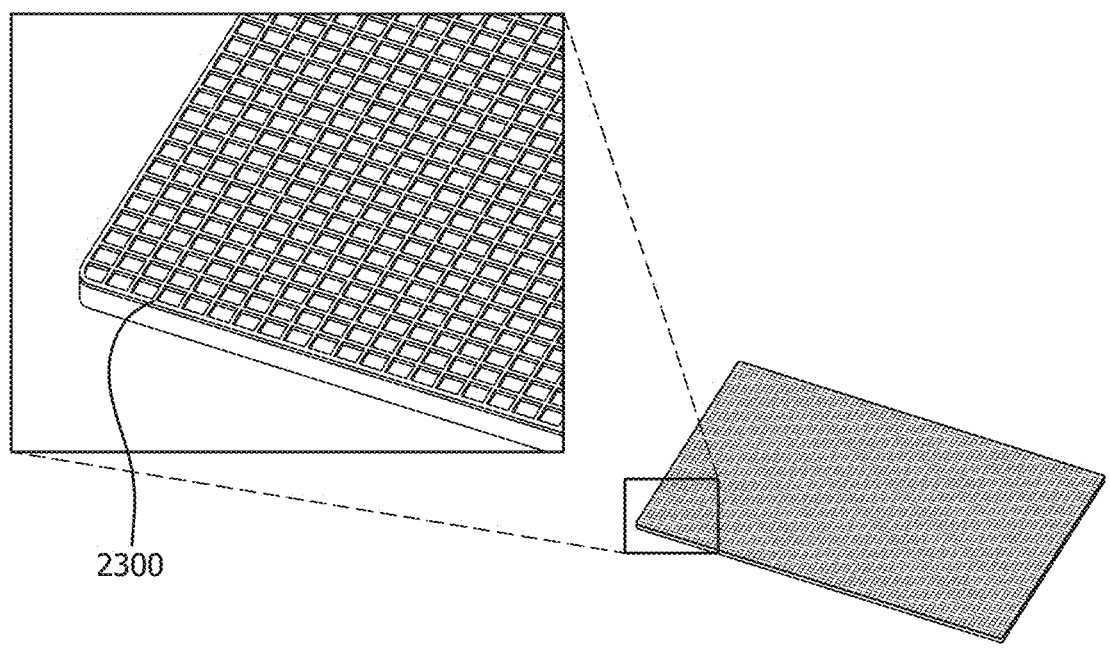
FIG. 23 shows a screen made from a bio-absorbable material according to embodiments described herein.

In some embodiments, one or both of the first and second composite layers is or includes a bio-absorbable material. The bio-absorbable material may be formed as a solid (molded, extruded, or crystals), a self-cohered web, a raised webbing, or a screen. In some embodiments, one or more layers of bio-absorbable material are attached to a non-bio-absorbable material having macroscopic porosity to avow for cell permeation (e.g., a cell permeable layer) to form a composite. In other embodiments, a non-bio-absorbable material having microscopic porosity to decrease or prevent cell permeation is releasably attached to the porous self-cohered web to permit atraumatic removal of the containment tube from the body of a patient days following implantation. Resorbing into the body can promote favorable type 1 collagen deposition, neovascularization, and a reduction of infection. FIG. 23 shows a screen 2300 made from a bio-absorbable material. Such a screen could be incorporated into a device as described herein to prevent "pillowing" of the device once the captive cells begin to multiply. In other examples, a bio-absorbable material could be incorporated into the cell encapsulation device as a powder. Non-limiting examples of suitable bio-absorbable materials include, but are not limited to, polyglycolide:trimethylene carbonate (PGA:TMC), polylactic acid, polyglycolic acid, poly (glycolide), poly(lactide-co-caprolactone), poly(caprolactone) poly(carbonates), poly(dioxanone), poly (hydroxybutyrates), poly(hydroxyvalerates), poly (hydroxybutyrates-co-valerates), and copolymers and blends thereof.

In some embodiments, incorporating bio-absorbable components into a cell encapsulation device helps to facilitate ease of implantation. For example, the bio-absorbable material may be temperature sensitive. In particular, the bio-absorbable material is much stiffer at colder temperatures and softens at higher temperatures (e.g., body temperature once implanted) so that the bio-absorbable material becomes more conformable and compliant after implantation. As a result the longitudinal strength formed of a bio-absorbable material may allow a clinician to place the cell encapsulation device in a patient with less effort and trauma to the host, and upon implantation, the bio-absorbable material becomes more conformable and compliant.

In some embodiments, the bio-absorbable material may have the capability to generate reactive oxygen species (ROS) at different levels in the body. ROS have been shown to promote various cell responses in the body, including, but not limited to, inhibiting or promoting cell proliferation, differentiation, migration, apoptosis, and angiogenesis. ROS generating materials can be made according to the teachings set forth in, for example, U.S. Pat. No. 9,259,435 to Brown, et al.

The cell encapsulation devices described herein are useful for holding cells in place in a tissue bed in a patient to allow the cells to provide biological therapy to a patient.

In some embodiments, the cells are introduced to the reservoir of the device through one or more ports. In some embodiments, the port extends through the sealed periphery between a first and second layer of a sealed membrane, so that the cells are introduced into a reservoir of the membrane through an edge of the membrane material.

In some embodiments, the cells are introduced in the form of a suspension or slurry in a medium. The cells may be individual cells, cell aggregates, or cell clusters. As one example, the medium may be a cell culture or cell growth medium, optionally including desired nutrients and/or other biomolecules. In some embodiments, insertion of the cells through the port may be accomplished using a syringe. In some embodiments, inserting the cells will apply pressure to the device, but the device will retain its general cross-sectional shape due to the structural spacers.

A cell encapsulation device as described herein may be implanted into a patient prior to or after insertion of cells into the device. For example, a cell encapsulation device may be inserted into a patient and allowed to vascularize such that vascular tissue grows into a vascularizing layer of the device. Cells may then be added while the device is in vivo. Alternatively, cells may be added to the cell encapsulation device prior to insertion of the device into a tissue bed of a patient.

Certain materials, such as, for example, perfluorocarbon emulsions, fluorohydrogels, silicone oils, silicone hydrogels, soybean oils, silicone rubbers, and polyvinyl chloride and combinations thereof are known to have high oxygen solubility. Such highly oxygen permeable materials provide enhanced transport of oxygen into the encapsulation device from the host tissue. Such materials can be utilized as the structural spacers, or may be applied, for example, as a coating or a filler onto the structural spacers.

Many of the materials used to construct a cell encapsulation device as described herein are inherently radio-opaque. Those materials that are not inherently radio-opaque can be modified to be radio-opaque by impregnation of the material with barium, for example. Other useful methods for rendering a material radio-opaque are known to those skilled in the art. The radio-opacity of materials used to construct a containment tube as described herein is mainly used to facilitate surgical placement of the cell encapsulation device or to locate the cell encapsulation device in a patient following implantation.

EXAMPLES

Example 1

An ePTFE membrane having two cell retentive (tight) layers separated by a vascularizing (open) layer, such as is depicted in FIG. 11, was obtained. Porous structural spacers formed of ePTFE connected the outer retentive layers and created reservoir spaces for housing cells therein. Two sheets of fluorinated ethylene propylene (FEP) film, each having a thickness of 4 mil (approximately 100 microns), were cut to form the peripheral seal of the cell encapsulation device. The cut FEP sheets were then stacked and aligned on the outer cell retentive surfaces of a 1"×2" (approximately 2.5 cm×5 cm) sample of the ePTFE membrane. A small area around the perimeter of the strips was protected with Kapton tape on both sides so that the perimeter would be left unbonded to allow for access to the interior chamber.

The ePTFE/FEP stack was then compressed by a silicone die at a pressure of 90 psi (approximately 6.2 bar or 620.5 kPA) and heated with an impulse heat band at a temperature of 375° C. for 30 seconds to allow the FEP film to melt and to weld the 3 layers of membrane together and create the periphery seal. The Kapton strip was removed and an FEP tube having dimensions of 0.047" (approximately 1.2 mm) (inner diameter)×0.059" (approximately 1.5 mm (outer diameter) was positioned over a 0.045" (approximately 1.1 mm) outer diameter steel mandrel and then inserted in the unbonded strip of the perimeter seal to provide access to the reservoir channels formed by the ePTFE structural supports. A heated handheld tip was heated to 330° C. and applied to the unbonded region to melt the FEP film on the perimeter to the FEP tube to complete the seal of the filling port to the device. The resulting encapsulation device is schematically depicted in FIG. 1.

Example 2

In this example, a thermoplastic polymer was used to create three dimensional structural supports having a patterned geometry. A cell retentive ePTFE membrane was restrained in a hoop. A patterned grid was placed on the surface of the ePTFE membrane to create a mask. The open area of the grid translated to the coverage area created by the thermoplastic structural supports. A fluorinated ethylene propylene (FEP) powder was uniformly applied to the restrained membrane covered with a mask by using a metal sieve. Metal sieves with both 150 micron and 710 micron openings were used. The FEP coating powder was fused and set by placing the coated ePTFE membrane in an oven at 300° C. for 10 min. The mask was then removed. The three dimensional structural support pillars remained on the surface of the cell retentive membrane.

Example 3

Samples A, B, C, and D, each approximately 1"×2" (approximately 2.5 cm×5 cm), were cut from a three-layer ePTFE composite that included an inner layer having structural spacers and two outer layers as defined in Table 1. The inner layer was positioned between two outer layers (i.e., one on each side of the inner layer). The membrane properties are listed Table 1.

TABLE 1

| | Area Weight (layered membrane) [g/m²] | Thickness (layered membrane) [mil] | ATEQ @ 12 mbar (layered membrane) [l/hr] | IPA Bubble Point (layered membrane) [psi] | Thickness (single outer layer) [mil] | IPA Bubble Point (single outer layer) [psi] | Area weight (single outer layer) [g/m²] | Thickness (middle layer) [mil] | Area weight (middle layer) [g/m²]] |
|---|---|---|---|---|---|---|---|---|---|
| Sample A | 47.8 | 14.6 | 14.5 | 21.8 | 0.75 | 27.5 | 11.95 | 13.1 | 23.9 |
| Sample B | 27.3 | 14.65 | 23 | 16.5 | 0.25 | 27.5 | 6.825 | 14.15 | 13.7 |
| Sample C | 93.7 | 16.55 | 9.5 | 32.9 | 1.15 | 32.9 | 28.11 | 14.25 | 37.5 |
| Sample D | 52.6 | 16.45 | 15.4 | 23 | 0.58 | 23 | 15.78 | 15.29 | 21.0 |

A die cut sheet of fluorinated ethylene propylene (FEP) film having a thickness of 4 mil (approximately 100 microns) was placed in parallel and adjacent to the outer layers of the membrane samples to form stacks. Each stack was then aligned with the device geometry outlined on a silicone die plate and impulse heat bonded. Periphery seals were formed by compressing the material stack along the desired seal geometry at 90 psi (approximately 6.2 bar or 620.5 kPA) and heating at 375° C. for 30 seconds.

Example 4

A sample approximately 1"×2" (approximately 2.5 cm×5 cm) was cut from a 3-layer ePTFE composite that included an inner layer having structural spacers and two outer layers. The inner layer was positioned between two outer layers (i.e., one on each side of the inner layer). The membrane properties are listed Table 2. A die cut sheet of fluorinated ethylene propylene (FEP) film having a thickness of 4 mil was placed in parallel and adjacent to the outer layers of the ePTFE composite membrane to form a stack. The stack was then aligned with the device geometry outlined on a silicone die plate and impulse heat bonded. A periphery seal was formed by compressing the stack, along the desired seal geometry, at 90 psi (approximately 6.2 bar or 620.5 kPA) and heating at 375° C. for 30 seconds. A port was formed by inserting an FEP tube 0.047" (approximately 1.2 mm) (inner diameter)×0.059" (approximately 1.5 mm (outer diameter) on a steel mandrel 0.045" (approximately 1.1 mm) between the outer layers of the ePTFE composite membrane at the distal gap of the seal geometry. HOTweezers thermal wire strippers Model M10 with a hand piece 4C modified with a 2.25 mm wire hole in the jaws (Meisei Corporation, Westlake Village, Calif.) heated to 330° C. for approximately 5 seconds were used to bond the planar periphery seal to FEP port. The steel mandrel was removed. The interior of the device was connected to the environment via the port.

Example 5

A multi-layer expanded PTFE (ePTFE) membrane was produced by combining layers of different membranes bonded together with a discontinuous fluoropolymer layer of fluorinated ethylene propylene (FEP). The first layer (tight layer) consists of a membrane with a smaller pore size and material properties listed in Table 3, processed based on the teachings of U.S. Pat. No. 3,953,566 to Gore. The second layer (open layer) consists of a larger pore size membrane produced based on the teachings of U.S. Pat. No. 5,814,405 to Branca, et al., where a discontinuous layer of FEP has been incorporated on the surface of this membrane based on the process teachings of International Patent Application Publication WO 94/13469 to Bacino while allowing this substrate to still be air permeable. The attributes of this open layer is listed in Table 3. The first layer (tight layer) was then put in contact with the second layer (open layer). The discontinuous FEP surface was located between the two PTFE layers as they were heated above the melting temperature of the FEP to create a bonded multilayer composite membrane with the final properties identified in Table 3. The ePTFE composite membrane was hydrophilically treated.

The larger pore size was 7.5 μm and the smaller pore size on the opposing side of the ePTFE composite membrane was 0.2 μm. The ePTFE composite membrane was arranged on a 3D printing machine (Makerbot Replicator 2X available from Makerbot Industries, Brooklyn, N.Y.) with the 0.2 μm pore side facing upwards.

A thin strand (approximately 1.75 mm) of a fluorothermoplastic terpolymer of tetrafluoroethylene (TFE), hexafluoropropylene (HFP), and vinylidene fluoride (VDF) was melted and printed onto the ePTFE composite membrane. The pattern was an perimeter bead arranged to enclose the entire area intended for cell retention except for one space which was left open for cell loading. Additionally, 5 internal lanes were printed to form 6 dead end wells. The

TABLE 2

| | Area Weight (layered membrane) [g/m²] | Thickness (layered membrane) [mil] | ATEQ @ 12 mbar (layered membrane) [l/hr] | IPA Bubble Point (layered membrane) [psi] | Thickness (single outer layer) [mil] | IPA Bubble Point (single outer layer) [psi] | Area weight (single outer layer) [g/m²] | Thickness (middle layer) [mil] | Area weight (middle layer) [g/m²]] |
|---|---|---|---|---|---|---|---|---|---|
| Example 4 | 93.7 | 16.55 | 9.5 | 32.9 | 1.15 | 32.9 | 28.11 | 14.25 | 37.5 | printed bead was approximately 300 µm in diameter. The overall dimension of the area intended to contain cells was 46 mm×50 mm. The lanes to form the dead end wells extended 40 mm from the 46 mm long edge leaving a gap of 10 mm to act as a distribution manifold.

The ePTFE composite membrane was placed on top of a 1/8" (approximately 3.2 mm) stainless steel sheet with the printed side facing up. A second ePTFE composite membrane identical to the first and having a pore size of 0.2 µm on one side and a pore size of 7.5 µm on the opposing side was arranged with the 0.2 µm pore size side facing down on the printed design. A stainless steel sheet having a thickness of 1/16" (approximately 1.6 mm) was placed on top of the stack of ePTFE composite membranes. Shims having a thickness of 254 µm were arranged around the printed area to limit the compression distance of the ePTFE membrane stack. The stainless steel sheets, the ePTFE membrane stack between them, were placed into a heated press (Wabash C30H-15-CPX from Wabash MPI, Wabash, Ind.) set at 400° F. (approximately 204° C.).

The press was closed, set to a pressure set point of 0.2 tons (182 kg), and held closed for 3 minutes. The press was then opened, the stainless steel stack containing the ePTFE membrane stack was removed and set on a metal table to cool. An aluminum weight of approximately 2 kg was placed on top of the stainless steel sheet to prevent distortion while cooling. Upon opening, it was observed that the two ePTFE membranes were bonded to the fluorothermoplastic terpolymer of TFE, HFP, and VDF to form an integral device suitable for cell encapsulation.

TABLE 3

| Layer | Mass/ area (g/m²) | Non-Contact Thickness (µm) | Bubble Point Pressure (psi) [~kPA] | Airflow (L/hr@12 mbar) | MD Force to Break (lbf/in) [~N/M] | TD Force to Break (lbf/in) [~N/M] |
| --- | --- | --- | --- | --- | --- | --- |
| First Layer Membrane | 13.20 | 34.1 | 51.80 [357.1] | 12.5 | 7.02 [1229] | 11.58 [2028] |
| Second layer membrane with discontinuous FEP | 5 (1.3 from FEP) | 34.1 | 1.70 [11.7] | | 3.87 [678] | 0.48 [84.1] |
| Final Multilayer Membrane | 17.90 | 73.4 | 52.10 [359.2] | 13.3 | 8.07 [1413] | 11.45 [2005] |

Example 6

The process of Example 5 was repeated with the exception that the printed pattern was a rectangle having a dimension of 12 mm×35 mm formed of a perimeter bead with a 2 mm spaced extension from one end to form a filling channel. The perimeter bead enclosed an array of printed fluorothermoplastic terpolymer of TFE, HFP, and VDF dots. The dots were approximately 300 µm in both diameter and height. 19 dots were printed on the ePTFE membrane and were arranged in a double row spaced 5 mm apart with 4 mm between sets of dots and a single row of dots centered between them spaced 4 mm apart off and set 2 mm form the double row. It was observed that upon removal of the stainless steel plates, the two ePTFE composite membranes were bonded to the fluorothermoplastic terpolymer of TFE, HFP, and VDF to form an integral device suitable for cell encapsulation. It was noted that the outer layer was not densified and remained porous for tissue ingrowth.

Example 7

The process of Example 5 was repeated with the exception that a perimeter bead was printed on the ePTFE composite membrane approximately 1 mm outside of the first perimeter bead. Prior to placing the second ePTFE composite membrane on the first, printed ePTFE composite membrane, a nitinol wire having a diameter of 10 mils (approximately 0.25 mm) shaped to fit between with beads was placed in between the two perimeter beads. Upon opening the stainless steel sheets, the nitinol wire was found to be encapsulated between the beads. The nitinol wire provided additional stiffness to the construction of the cell encapsulation device and functioned as a structural spacer. The printed terpolymer also functioned as a structural spacer.

Example 8

A multi-layer expanded PTFE (ePTFE) membrane was produced by combining layers of different membranes bonded together with a discontinuous fluoropolymer layer of fluorinated ethylene propylene (FEP). The first layer (tight layer) consists of a membrane with a smaller pore size and material properties listed in Table 3, processed based on the teachings of U.S. Pat. No. 3,953,566 to Gore. The second layer (open layer) consists of a larger pore size membrane produced based on the teachings of U.S. Pat. No. 5,814,405 to Branca, et al., where a discontinuous layer of FEP has been incorporated on the surface of this membrane based on the process teachings of International Patent Application Publication WO 94/13469 to Bacino while allowing this substrate to still be air permeable. The attributes of this open layer is listed in Table 3. The first layer (tight layer) was then put in contact with the second layer (open layer). The discontinuous FEP surface was located between the two PTFE layers as they were heated above the melting temperature of the FEP to create a bonded multilayer composite membrane with the final properties identified in Table 3. The ePTFE composite membrane was hydrophilically treated.

The larger pore size was 7.5 µm and the smaller pore size on the opposing side of the ePTFE composite membrane was 0.2 µm. The ePTFE composite membrane was arranged on a 3D printing machine (Makerbot Replicator 2X available from Makerbot Industries, Brooklyn, N.Y.) with the 0.2 µm pore side facing upwards.

A thin strand (approximately 1.75 mm) of a fluorothermoplastic terpolymer of tetrafluoroethylenen (TFE), hexafluorofluoropropylene (HFP), and vinylidene fluoride (VDF) was melted and printed onto the ePTFE composite membrane. The pattern was 7 dots arranged 3 down the center and spaced 6 mm apart and a double row of dots spaced 3 mm apart and 6 mm between sets of dots.

The ePTFE composite membrane was placed on top of a 1/8" stainless steel sheet with the printed side facing upwards. A die cut fluorothermoplastic terpolymer of TFE-HFP-VDF having a thickness of 5 mil (approximately 0.13 mm) was placed on the printed side of the ePTFE composite membrane. A second ePTFE composite membrane identical to the first and having a pore size of 0.2 µm on one side and a pore size of 7.5 µm on the opposing side was arranged with the 0.2 µm pore size side facing down on the TFE-HFP-VDF terpolymer film.

An additional layer of a fluorothermoplastic terpolymer of TFE-HFP-VDF film having a thickness of 5 mil (approximately 0.13 mm) was placed on the outside of each ePTFE composite membrane and sealed in place using an impulse heat sealer (Packworld model AO4-2565 Nazareth, Pa.). The unattached surface of each dot was bonded to the interior of the ePTFE composite membrane by lightly touching it with a soldering iron set at 550° F. (approximately 288° C.) to form a device capable of cell encapsulation.

Example 9

Figure 24:
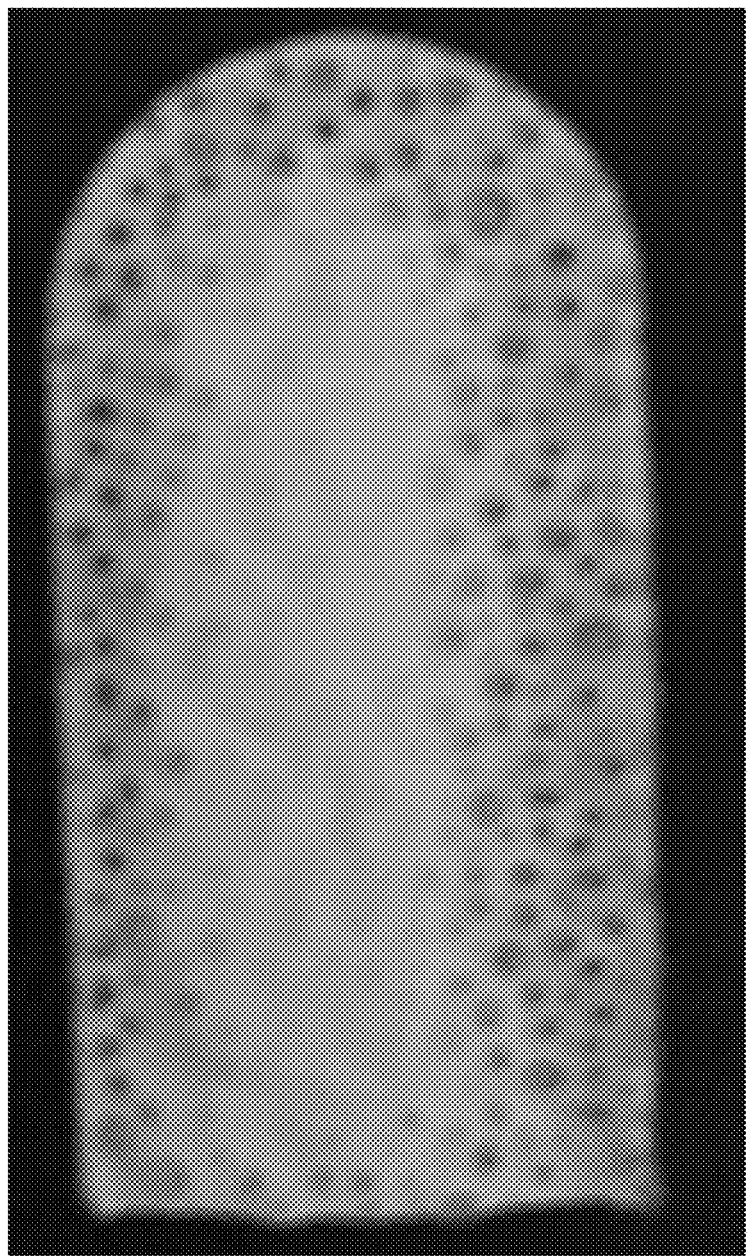
FIG. 24 is a photograph showing the top view of a cell encapsulation device produced in Example 9 according to embodiments described herein.

The procedure set forth in Example 1 was repeated with the exception that ePTFE membranes obtained by the process set forth in U.S. Pat. No. 8,808,848 to Bacino, et al. were obtained and used to form a structure having two cell retentive (tight) layers separated by a vascularizing (open) layer. Structural spacers formed of perfluoroalkoxy alkane (PFA) beads connected the outer retentive layers and created reservoir spaces for housing cells therein. The resulting encapsulation device is shown in FIG. 24.

Example 10

The ePTFE membrane used was for this Example was identical to the ePTFE membrane utilized in Example 2. The ePTFE membrane was arranged on the silicone die of an impulse heat sealer (Packworld Model AO4-2565) with the three dimensional structural support pillars of the cell retentive membrane facing upwards. A die cut sheet of 5 mil (approximately 0.13 mm) thick fluorothermoplastic polymerized (i.e., a fluorothermoplastic terpolymer of tetrafluoroethylene (TFE), hexafluoropropylene (HFP), and vinylidene fluoride (VDF) was placed adjacent to the cell retentive membrane and aligned with the device geometry outline on the silicone die plate.

A periphery seal was formed by compressing the stack along the desired seal geometry at 30 psi (approximately 2 bar or 206.8 kPA) and heating at 280° C. for 30 seconds. The stack was then rotated 90° so that the remaining unbonded area of the fluorothermoplastic film was adjacent to the impulse heat seal band. The completion of the periphery seal was formed by compressing the stack at 30 psi (approximately 2 bar or 206.8 kPA) and heating at 280° C. for 30 seconds.

The excess material outside of the periphery seal was die cut and removed with a steel rule die. A cell encapsulation device was constructed that provides an internal spacing for containing cells by using a three dimensional structural pattern that created with a thermoplastic polymer.

Example 11

A compression mold was fabricated to make a three-dimensional molded insert. The molded insert was constructed by placing a sufficient quantity of a thermoplastic polymer (i.e., a fluorothermoplastic terpolymer of tetrafluoroethylene (TFE), hexafluoropropylene (HFP), and vinylidene fluoride (VDF)) into the mold and placing the filled mold into a heated press (Wabash C30H-15-CPX) set at 400° F. (approximately 204° C.) for a 5 minute pre-heat. The press was then closed to a pressure set point of 0.2 tons (approximately 182 kg) and held closed for 1 minute. The press was then opened, and the mold was set aside to cool until the finished molded insert could be removed and trimmed of any excess polymer.

A multi-layer expanded PTFE (ePTFE) membrane was produced by combining layers of different membranes bonded together with a discontinuous fluoropolymer layer of fluorinated ethylene propylene (FEP). The first layer (tight layer) consists of a membrane with a smaller pore size and material properties listed in Table 3, processed based on the teachings of U.S. Pat. No. 3,953,566 to Gore. The second layer (open layer) consists of a larger pore size membrane produced based on the teachings of U.S. Pat. No. 5,814,405 to Branca, et al., where a discontinuous layer of FEP has been incorporated on the surface of this membrane based on the process teachings of International Patent Application Publication WO 94/13469 to Bacino while allowing this substrate to still be air permeable. The attributes of this open layer is listed in Table 3. The first layer (tight layer) was then put in contact with the second layer (open layer). The discontinuous FEP surface was located between the two PTFE layers as they were heated above the melting temperature of the FEP to create a bonded multilayer composite membrane with the final properties identified in Table 3. The first layer (tight layer) was then put in contact with the second layer (open layer). The discontinuous FEP surface was located between the two PTFE layers as they were heated above the melting temperature of the FEP to create a bonded multilayer composite membrane with the final properties identified in Table 3. The ePTFE composite membrane was hydrophilically treated.

The ePTFE composite membrane was arranged on the silicone die of an impulse heat sealer (Packworld Model AO4-2565) with the cell retentive (tight) membrane facing upwards. A die cut sheet of 5 mil (approximately 0.13 mm) thick fluorothermoplastic polymerized TFE-HFP-VDF terpolymer was placed adjacent to the cell retentive (tight) membrane and aligned with the device geometry outline on the silicone die plate. The molded insert was placed inside the die cut opening of the fluorothermoplastic film. A second ePTFE composite membrane identical to the first was placed on top of the molded insert with the open layer facing upwards.

A periphery seal was formed by compressing the stack along the desired seal geometry at 30 psi (approximately 2 bar or 206.8 kPA) and heating at 280° C. for 30 seconds. The unattached surface of each pillar of the molded insert was bonded to the interior of the ePTFE composite membrane by lightly touching it with a soldering iron set at 550° F. (approximately 288° C.).

The stack was then rotated 90° so that the remaining unbonded area of the fluorothermoplastic TFE-HFP-VDF terpolymer film was adjacent to the impulse heat seal band. The completion of the periphery seal was formed by compressing the stack at 30 psi (approximately 2 bar or 206.8 kPA) and heating at 280° C. for 30 seconds.

The excess material outside of the periphery seal was die cut and removed with a steel rule die. The resulting encapsulation device is shown in FIG. 25.

Example 12

Pressure deflection of cell encapsulation devices described herein were characterized using a non-contact surface scanning method (Keyence VR-3000 3D Macroscope).

Figure 26:
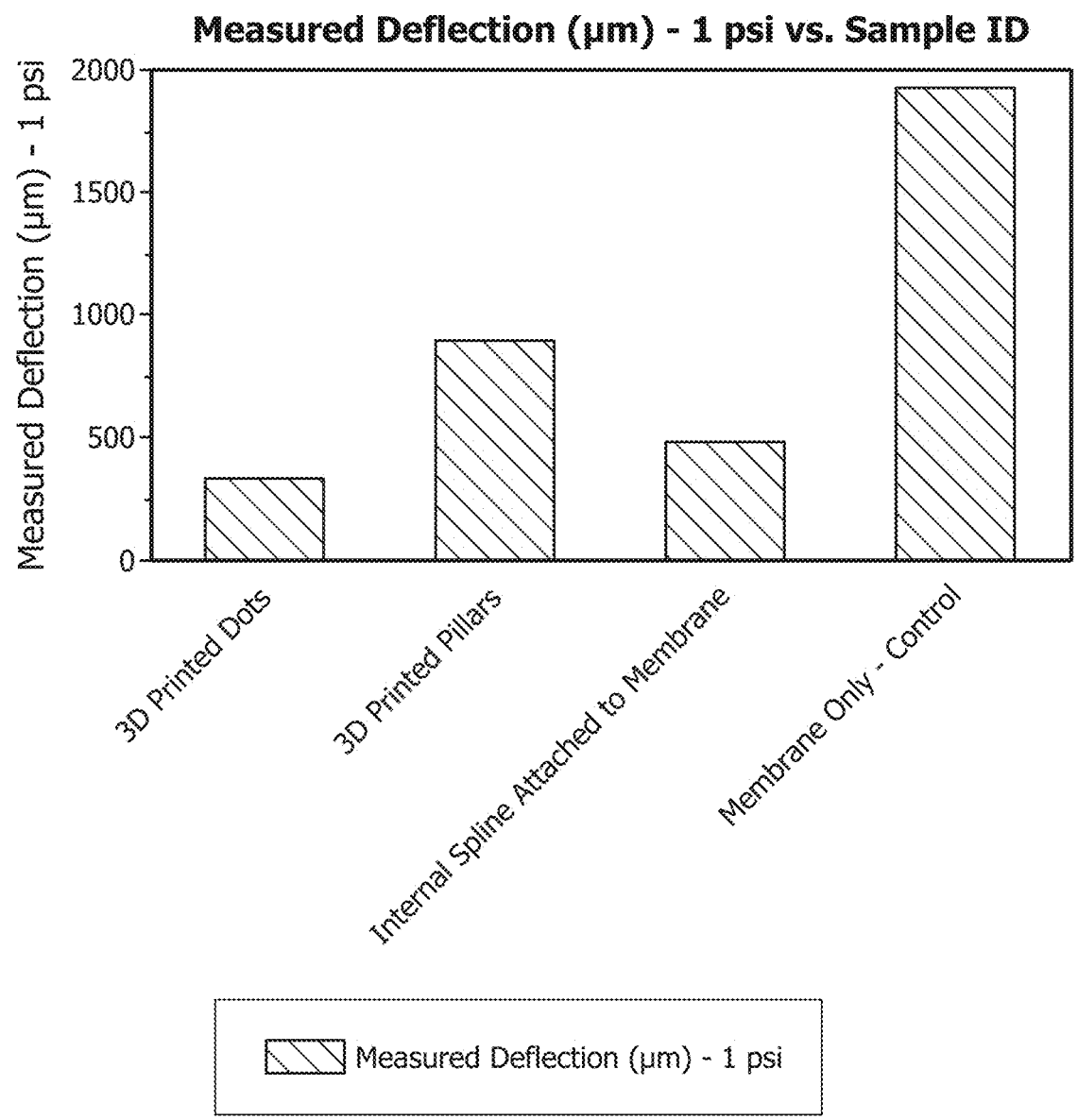
FIG. 26 is a graphical illustration depicting the pressure deflection of various cell encapsulation devices according to embodiments described herein.

Sample cell encapsulation devices were attached to a blunt needle and affixed to a custom, 3D printed via stereolithography, fixture to stabilize the sample for evaluation. The sample surfaces of each device were each wet out with an IPA/H20 solution prior to pressurization. Sample devices were pressurized to 1 psi (approximately 0.3 bar or 6.9 kPA), and the deflection (i.e., distance from the ePTFE membrane to the center of device lumen) was measured. Data was generated across a variety of sample cell encapsulation devices with structural supports and reservoirs for comparison to a control sample. The data is depicted in FIG. 26. It was determined that the addition of internal structural supports and/or reservoirs clearly minimized the deflection (distance from the ePTFE membrane to the center of the device lumen) as compared to a device without any internal support.

The invention of this application may also be described by the following:

1. A cell encapsulation device comprising:
a first layer sealed along a portion of its periphery to a second layer along a portion of its periphery to define a chamber comprising a first interior surface and an opposing second interior surface, wherein the first interior surface is spaced apart in the chamber from the second interior surface; and
structural spacers disposed in the chamber to maintain an average distance between the first interior surface and the second interior surface along a length and/or width of the chamber, wherein the structural spacers further define at least one reservoir space for the placement of cells within the chamber.

2. The cell encapsulation device of claim 1,
further comprising at least one port in fluid communication with the reservoir space; or
further comprising a plurality of cells in said at least one reservoir space; or
wherein the first and second layers are impervious to cell ingrowth; or
wherein said structural spacers comprise an oxygen permeable material; or
wherein said encapsulation device has a substantially tubular configuration; or
wherein the structural spacers maintain the average distance under an applied force; or
wherein the structural spacers comprise a porous material; or
wherein the structural spacers comprise a shape memory material; or
wherein the average distance between the first and second interior surfaces is at least about 50 microns; or
wherein the device comprises a plurality of reservoir spaces that are interconnected; or
wherein the device comprises at least two reservoir spaces that are discrete; or
wherein the structural spacers comprise a plurality of fibers; or
wherein the structural spacers comprise a 3D printed bead of a thermoplastic polymer; or
wherein the structural spacers comprise a three dimensional woven fabric comprising a structural restraint.

3. The cell encapsulation device of claim 1, wherein at least one of the first and second layers is a composite layer comprising:
a) an outer porous layer; and
b) an inner porous layer adjacent to the outer porous layer, wherein the inner porous layer has a porosity that is less than the outer porous layer, and wherein a portion of the inner porous layer is the first or second interior surface.

4. The cell encapsulation device of claim 3, wherein both of the first and second layers are composite layers.

5. The cell encapsulation device of claim 4,
wherein the outer porous layer is sufficiently porous to permit growth of vascular tissue from a patient within the pores of the outer porous layer up to, but not through, the inner porous layer; or
wherein the inner porous layer is impervious to cellular ingrowth; or
wherein at least one of said inner porous layer and said outer porous layer comprises expanded polytetrafluoroethylene.

6. The cell encapsulation device of claim 1, wherein at least one of the first and second layers comprises a bio-absorbable material.

7. The cell encapsulation device of claim 6,
wherein the bio-absorbable material is in the form of a powder; or
wherein the bio-absorbable material is in the form of a screen.

8. The cell encapsulation device of claim 4, wherein the structural spacers are adhered to the inner porous layers of the first and second composite layers.

9. The cell encapsulation device of claim 8, wherein the adhered structural spacers do not penetrate into the pores of the inner porous layers of the first and second composite layers.

10. The cell encapsulation device of claim 1, wherein the structural spacers comprise a non-porous material.

11. The cell encapsulation device of claim 10, wherein the non-porous material comprises fluorinated ethylene propylene, tetrafluoroethylene-(perfluoroalkyl) vinyl ether, polytetrafluoroethylene, polyurethane, polyvinylidene fluoride, and combinations hereof.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A cell encapsulation device comprising:
a first layer sealed along a portion of its periphery to a second layer along a portion of its periphery to define a chamber comprising a first interior surface and an opposing second interior surface, wherein the first interior surface is spaced apart in the chamber from the second interior surface;
structural spacers disposed within the chamber to maintain an average distance between the first interior surface and the second interior surface along a length and/or width of the chamber and to interconnect said first interior surface and said second interior surface and,
at least one reservoir space for the placement of cells within the chamber,
wherein the structural spacers maintain the average distance both under external compressive forces and under internal expansive forces.

2. The cell encapsulation device of claim 1, further comprising at least one port in fluid communication with the reservoir space.

3. The cell encapsulation device of claim 1, wherein the at least one reservoir space is configured to receive a plurality of cells.

4. The cell encapsulation device of claim 1, wherein the first and second layers are impervious to cell ingrowth.

5. The cell encapsulation device of claim 1, wherein at least one of the first and second layers is a composite layer comprising:
a) an outer porous layer; and
b) an inner porous layer adjacent to the outer porous layer, wherein the inner porous layer has a porosity that is less than the outer porous layer, and wherein a portion of the inner porous layer is the first or second interior surface.

6. The cell encapsulation device of claim 5, wherein both of the first and second layers are composite layers.

7. The cell encapsulation device of claim 6, wherein the outer porous layer is sufficiently porous to permit growth of vascular tissue from a patient within the pores of the outer porous layer up to, but not through, the inner porous layer.

8. The cell encapsulation device of claim 6, wherein the inner porous layer is impervious to cellular ingrowth.

9. The cell encapsulation device of claim 6, wherein the structural spacers are adhered to the inner porous layers of the first and second composite layers.

10. The cell encapsulation device of claim 9, wherein the structural spacers are adhered via an adhesive and the adhesive does not penetrate into the pores of the outer porous layers of the first and second composite layers.

11. The cell encapsulation device of claim 6, wherein at least one of said inner porous layer and said outer porous layer comprises expanded polytetrafluoroethylene.

12. The cell encapsulation device of claim 1, wherein at least one of the first and second layers comprises a bio-absorbable material.

13. The cell encapsulation device of claim 12, wherein the bio-absorbable material is in the form of a powder or a screen.

14. The cell encapsulation device of claim 1, wherein said structural spacers comprise an oxygen permeable material.

15. The cell encapsulation device of claim 1, wherein said cell encapsulation device has a substantially tubular configuration.

16. The cell encapsulation device of claim 1, wherein the structural spacers maintain the average distance under an applied force.

17. The cell encapsulation device of claim 1, wherein the structural spacers comprise a porous material.

18. The cell encapsulation device of claim 1, wherein the structural spacers comprise a shape memory material.

19. The cell encapsulation device of claim 1, wherein the structural spacers comprise an oxygen permeable material.

20. The cell encapsulation device of claim 1, wherein the structural spacers comprise a non-porous material.

21. The cell encapsulation device of claim 1, wherein the average distance between the first and second interior surfaces is at least about 50 microns.

22. The cell encapsulation device of claim 1, wherein the device comprises a plurality of reservoir spaces that are interconnected.

23. The cell encapsulation device of claim 1, wherein the device comprises at least two reservoir spaces that are discrete.

24. The cell encapsulation device of claim 1, wherein the structural spacers comprise a plurality of fibers.

25. The cell encapsulation device of claim 1, wherein the structural spacers comprise a 3D printed bead of a thermoplastic polymer.

26. The cell encapsulation device of claim 1, wherein the structural spacers comprise a three dimensional woven fabric comprising a structural restraint.

27. A cell encapsulation device comprising:
a first layer sealed along a portion of its periphery to a second layer along a portion of its periphery to define a chamber comprising a first interior surface and an opposing second interior surface, wherein the first interior surface is spaced apart in the chamber from the second interior surface;
structural spacers disposed within the chamber to maintain an average distance between the first interior surface and the second interior surface; and
at least one reservoir space for the placement of cells within the chamber,
wherein the first and second layers are each composite layers that comprise:
a) an outer porous layer; and
b) an inner porous layer adjacent to the outer porous layer, wherein the inner porous layer has a porosity that is less than the outer porous layer, and wherein a portion of the inner porous layer is the first or second interior surface, and
wherein the structural spacers are adhered to at least one of the inner porous layers of the first and second composite layers via an adhesive and the adhesive does not penetrate into the pores of the outer porous layers of the first and second composite layers.

28. The cell encapsulation device of claim 27, further comprising at least one port in fluid communication with the reservoir space.

29. The cell encapsulation device of claim 27, wherein the at least one reservoir space is configured to receive a plurality of cells.

30. The cell encapsulation device of claim 27, wherein the first and second layers are impervious to cell ingrowth.

31. The cell encapsulation device of claim 27, wherein the outer porous layer is sufficiently porous to permit growth of vascular tissue from a patient within the pores of the outer porous layer up to, but not through, the inner porous layer.

32. The cell encapsulation device of claim 27, wherein at least one of the first and second layers comprises a bio-absorbable material.

33. The cell encapsulation device of claim 32, wherein the bio-absorbable material is in the form of a powder or a screen.

34. The cell encapsulation device of claim 27, wherein said structural spacers comprise an oxygen permeable material.

35. The cell encapsulation device of claim 27, wherein the inner porous layer is impervious to cellular ingrowth.

36. The cell encapsulation device of claim 27, wherein said cell encapsulation device has a substantially tubular configuration.

37. The cell encapsulation device of claim 27, wherein the structural spacers maintain the average distance under an applied force.

38. The cell encapsulation device of claim 27, wherein the structural spacers comprise a porous material.

39. The cell encapsulation device of claim 27, wherein the structural spacers comprise a shape memory material.

40. The cell encapsulation device of claim 27, wherein the structural spacers comprise an oxygen permeable material.

41. The cell encapsulation device of claim 27, wherein the structural spacers comprise a non-porous material.

42. The cell encapsulation device of claim 27, wherein the average distance between the first and second interior surfaces is at least about 50 microns.

43. The cell encapsulation device of claim 27, wherein the device comprises a plurality of reservoir spaces that are interconnected.

44. The cell encapsulation device of claim 27, wherein the device comprises at least two reservoir spaces that are discrete.

45. The cell encapsulation device of claim 27, wherein at least one of said inner porous layer and said outer porous layer comprises expanded polytetrafluoroethylene.

46. The cell encapsulation device of claim 27, wherein the structural spacers comprise a plurality of fibers.

47. The cell encapsulation device of claim 27, wherein the structural spacers comprise a 3D printed bead of a thermoplastic polymer.

48. The cell encapsulation device of claim 27, wherein the structural spacers comprise a three dimensional woven fabric comprising a structural restraint.

49. A cell encapsulation device comprising:
- a first layer sealed along a portion of its periphery to a second layer along a portion of its periphery to define a chamber comprising a first interior surface and an opposing second interior surface, wherein the first interior surface is spaced apart in the chamber from the second interior surface;
- structural spacers disposed within the chamber to maintain an average distance between the first interior surface and the second interior surface along a length and/or width of the chamber and to interconnect said first interior surface and said second interior surface, the structural spacers each having a height and a width, and
- two or more reservoir spaces for the placement of cells within the chamber,
- wherein the structural spacers are adhered to at least one of the first interior surface and the second interior surface.

50. The cell encapsulation device of claim 49, further comprising at least one port in fluid communication with the reservoir space.

51. The cell encapsulation device of claim 49, wherein the reservoir spaces are interconnected.

52. The cell encapsulation device of claim 49, wherein the structural spacers comprise a porous material.

53. The cell encapsulation device of claim 49, wherein the structural spacers comprise a shape memory material.

54. The cell encapsulation device of claim 49, wherein the structural spacers comprise an oxygen permeable material.

55. The cell encapsulation device of claim 49, wherein the structural spacers comprise a non-porous material.

56. The cell encapsulation device of claim 49, wherein the structural spacers comprise a plurality of fibers.

57. The cell encapsulation device of claim 49, wherein the structural spacers comprise a 3D printed bead of a thermoplastic polymer.

58. The cell encapsulation device of claim 49, wherein the structural spacers maintain the average distance under an applied force.

59. The cell encapsulation device of claim 49, wherein the device comprises a plurality of reservoir spaces that are interconnected.

60. The cell encapsulation device of claim 49, wherein the device comprises at least two reservoir spaces that are discrete.

61. The cell encapsulation device of claim 49, wherein the structural spacers comprise a three dimensional woven fabric comprising a structural restraint.

62. The cell encapsulation device of claim 49, wherein the inner layers are impervious to cell ingrowth.

63. The cell encapsulation device of claim 62, wherein the outer porous layer is sufficiently porous to permit growth of vascular tissue from a patient within the pores of the outer porous layer up to, but not through, the inner porous layer.

64. The cell encapsulation device of claim 49, wherein at least one of said inner porous layer and said outer porous layer comprises expanded polytetrafluoroethylene.

65. The cell encapsulation device of any one of claim 49, wherein the first and second layers are each composite layers that comprise:
a) an outer porous layer; and
b) an inner porous layer adjacent to the outer porous layer, wherein the inner porous layer has a porosity that is less than the outer porous layer, and wherein a portion of the inner porous layer is the first or second interior surface.

66. The cell encapsulation device of claim 49, wherein the structural spacers are adhered via an adhesive and the adhesive does not penetrate into the pores of the outer porous layers of the first and second composite layers.

67. The cell encapsulation device of claim 49, wherein the height is greater than the base.

68. The cell encapsulation device of claim 49, wherein the base is greater than the height.

69. The cell encapsulation device of claim 49, wherein the structural spacers are molded inserts with three dimensional pillars.

70. The cell encapsulation device of claim 49, wherein the structural spacers have a height to base aspect ratio from 1/5 to 10/1.

71. The cell encapsulation device of claim 49, wherein the structural spacers are molded inserts with three dimensional pillars.

* * * * *